(12) United States Patent
Trieu et al.

(10) Patent No.: US 8,221,465 B2
(45) Date of Patent: Jul. 17, 2012

(54) MULTI-CHAMBER EXPANDABLE INTERSPINOUS PROCESS SPACER

(75) Inventors: Hai H. Trieu, Cordova, TN (US); Kent M. Anderson, Mountain View, CA (US); Eric C. Lange, Pleasanton, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 113 days.

(21) Appl. No.: 12/795,883

(22) Filed: Jun. 8, 2010

(65) Prior Publication Data

US 2010/0249841 A1  Sep. 30, 2010

Related U.S. Application Data

(62) Division of application No. 11/413,587, filed on Apr. 28, 2006.

(51) Int. Cl.
  *A61B 17/70* (2006.01)
(52) U.S. Cl. ...................................................... 606/249
(58) Field of Classification Search .......... 606/248–249; 623/17.11–17.16
  See application file for complete search history.

(56) References Cited

U.S. PATENT DOCUMENTS

| | | |
|---|---|---|
| 1,870,942 A | 8/1932 | Beatty |
| 2,677,369 A | 5/1954 | Knowles |
| 3,108,595 A | 10/1963 | Overment |
| 3,397,699 A | 8/1968 | Kohl |
| 3,648,691 A | 3/1972 | Lumb et al. |
| 3,867,728 A | 2/1975 | Stubstad et al. |
| 4,011,602 A | 3/1977 | Rybicki et al. |
| 4,257,409 A | 3/1981 | Bacal et al. |
| 4,327,736 A | 5/1982 | Inoue |
| 4,554,914 A | 11/1985 | Kapp et al. |
| 4,573,454 A | 3/1986 | Hoffman |
| 4,573,966 A | 3/1986 | Weikl et al. |
| 4,604,995 A | 8/1986 | Stephens et al. |
| 4,610,662 A | 9/1986 | Weikl et al. |
| 4,686,970 A | 8/1987 | Dove et al. |
| 4,721,103 A | 1/1988 | Freedland |
| 4,827,918 A | 5/1989 | Olerud |
| 4,932,975 A | 6/1990 | Main et al. |
| 4,969,888 A | 11/1990 | Scholten et al. |
| 5,011,484 A | 4/1991 | Breard |
| 5,019,042 A | 5/1991 | Sahota |
| 5,047,055 A | 9/1991 | Bao et al. |

(Continued)

FOREIGN PATENT DOCUMENTS

DE  2821678 A1  11/1979

(Continued)

OTHER PUBLICATIONS

"Dispositivo Intervertebrale Ammortizzante DIAM," date unknown, p. 1.

(Continued)

*Primary Examiner* — Eduardo C Robert
*Assistant Examiner* — Jerry Cumberledge

(57) ABSTRACT

An expandable interspinous process spacer is disclosed that includes at least two chambers, one disposed within the other. Each of the at least two chambers can receive an injectable biocompatible material, which advantageously may have different material properties such as hardness. Further, the expandable interspinous process spacer can be changed from a deflated configuration to an inflated configuration. In the inflated configuration, the expandable interspinous process spacer can engage and support a superior spinous process and an inferior spinous process.

6 Claims, 22 Drawing Sheets

U.S. PATENT DOCUMENTS

| | | |
|---|---|---|
| 5,092,866 A | 3/1992 | Breard et al. |
| 5,112,306 A | 5/1992 | Burton et al. |
| 5,171,280 A | 12/1992 | Baumgartner |
| 5,201,734 A | 4/1993 | Cozad et al. |
| 5,306,275 A | 4/1994 | Bryan |
| 5,316,422 A | 5/1994 | Coffman |
| 5,330,429 A | 7/1994 | Noguchi et al. |
| 5,342,305 A | 8/1994 | Shonk |
| 5,358,487 A | 10/1994 | Miller |
| 5,360,430 A | 11/1994 | Lin |
| 5,366,455 A | 11/1994 | Dove |
| 5,415,661 A | 5/1995 | Holmes |
| 5,437,672 A | 8/1995 | Alleyne |
| 5,454,812 A | 10/1995 | Lin |
| 5,460,610 A | 10/1995 | Don Michael |
| 5,480,442 A | 1/1996 | Bertagnoli |
| 5,496,318 A | 3/1996 | Howland et al. |
| 5,549,679 A | 8/1996 | Kuslich |
| 5,562,736 A | 10/1996 | Ray et al. |
| 5,609,634 A | 3/1997 | Voydeville |
| 5,628,756 A | 5/1997 | Barker, Jr. et al. |
| 5,645,597 A | 7/1997 | Krapiva |
| 5,645,599 A | 7/1997 | Samani |
| 5,674,295 A | 10/1997 | Ray et al. |
| 5,676,702 A | 10/1997 | Ratron |
| 5,690,649 A | 11/1997 | Li |
| 5,702,452 A | 12/1997 | Argenson et al. |
| 5,702,454 A | 12/1997 | Baumgartner |
| 5,746,762 A | 5/1998 | Bass |
| 5,800,549 A | 9/1998 | Bao et al. |
| 5,810,815 A | 9/1998 | Morales |
| 5,836,948 A | 11/1998 | Zucherman et al. |
| 5,860,977 A | 1/1999 | Zucherman et al. |
| 5,964,730 A | 10/1999 | Williams et al. |
| 5,976,186 A | 11/1999 | Bao et al. |
| 6,022,376 A | 2/2000 | Assell et al. |
| 6,048,342 A | 4/2000 | Zucherman et al. |
| 6,066,154 A | 5/2000 | Reiley et al. |
| 6,068,630 A | 5/2000 | Zucherman et al. |
| 6,074,390 A | 6/2000 | Zucherman et al. |
| 6,102,922 A | 8/2000 | Jakobsson et al. |
| 6,132,464 A | 10/2000 | Martin |
| 6,214,037 B1 | 4/2001 | Mitchell et al. |
| 6,245,107 B1 | 6/2001 | Ferree |
| 6,293,949 B1 | 9/2001 | Justis et al. |
| 6,336,930 B1 | 1/2002 | Stalcup et al. |
| 6,352,537 B1 | 3/2002 | Strnad |
| 6,364,883 B1 | 4/2002 | Santilli |
| 6,402,750 B1 | 6/2002 | Atkinson et al. |
| 6,419,703 B1 | 7/2002 | Fallin et al. |
| 6,419,704 B1 | 7/2002 | Ferree |
| 6,432,130 B1 | 8/2002 | Hanson |
| 6,440,169 B1 | 8/2002 | Elberg et al. |
| 6,451,019 B1 | 9/2002 | Zucherman et al. |
| 6,500,178 B2 | 12/2002 | Zucherman et al. |
| 6,514,256 B2 | 2/2003 | Zucherman et al. |
| 6,582,433 B2 | 6/2003 | Yun |
| 6,610,069 B2 | 8/2003 | Euteneuer et al. |
| 6,626,944 B1 * | 9/2003 | Taylor ........................ 623/17.16 |
| 6,645,207 B2 | 11/2003 | Dixon et al. |
| 6,669,729 B2 | 12/2003 | Chin |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,733,533 B1 | 5/2004 | Lozier |
| 6,733,534 B2 * | 5/2004 | Sherman ...................... 623/17.16 |
| 6,761,720 B1 | 7/2004 | Senegas |
| 6,835,205 B2 | 12/2004 | Atkinson et al. |
| 6,902,580 B2 | 6/2005 | Fallin et al. |
| 6,946,000 B2 | 9/2005 | Senegas et al. |
| 6,958,077 B2 * | 10/2005 | Suddaby ...................... 623/17.11 |
| 6,969,404 B2 | 11/2005 | Ferree |
| 7,041,136 B2 | 5/2006 | Goble et al. |
| 7,048,736 B2 | 5/2006 | Robinson et al. |
| 7,081,120 B2 | 7/2006 | Li et al. |
| 7,087,083 B2 | 8/2006 | Pasquet et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,442,208 B2 | 10/2008 | Mathieu et al. |
| 7,442,210 B2 | 10/2008 | Segal et al. |
| 7,445,637 B2 | 11/2008 | Taylor |
| 7,582,106 B2 | 9/2009 | Teitelbaum et al. |
| 7,604,652 B2 | 10/2009 | Arnin et al. |
| 7,658,752 B2 | 2/2010 | Labrom et al. |
| 7,666,205 B2 | 2/2010 | Weikel et al. |
| 7,749,252 B2 | 7/2010 | Zucherman et al. |
| 7,771,456 B2 | 8/2010 | Hartman et al. |
| 7,824,431 B2 | 11/2010 | McCormack |
| 7,862,615 B2 | 1/2011 | Carli et al. |
| 7,901,430 B2 | 3/2011 | Matsuura et al. |
| 7,942,847 B2 | 5/2011 | Stupecky et al. |
| 2001/0016743 A1 | 8/2001 | Zucherman et al. |
| 2002/0082600 A1 * | 6/2002 | Shaolian et al. ................ 606/61 |
| 2002/0143331 A1 | 10/2002 | Zucherman et al. |
| 2002/0177866 A1 | 11/2002 | Weikel et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0064094 A1 | 4/2004 | Freyman |
| 2004/0083002 A1 | 4/2004 | Belef et al. |
| 2004/0097931 A1 | 5/2004 | Mitchell |
| 2004/0106995 A1 | 6/2004 | LeCouedic et al. |
| 2004/0117017 A1 | 6/2004 | Pasquet et al. |
| 2004/0133280 A1 | 7/2004 | Trieu |
| 2004/0199255 A1 | 10/2004 | Mathieu et al. |
| 2004/0260239 A1 | 12/2004 | Kusleika |
| 2005/0010293 A1 | 1/2005 | Zucherman et al. |
| 2005/0015140 A1 | 1/2005 | deBeer |
| 2005/0033434 A1 | 2/2005 | Berry |
| 2005/0049708 A1 | 3/2005 | Atkinson et al. |
| 2005/0056292 A1 | 3/2005 | Cooper |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0228391 A1 | 10/2005 | Levy et al. |
| 2005/0261768 A1 | 11/2005 | Trieu |
| 2005/0267579 A1 | 12/2005 | Reiley et al. |
| 2005/0288672 A1 | 12/2005 | Ferree |
| 2006/0004447 A1 | 1/2006 | Mastrorio et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0122620 A1 | 6/2006 | Kim |
| 2006/0129239 A1 | 6/2006 | Kwak |
| 2006/0136060 A1 | 6/2006 | Taylor |
| 2006/0149136 A1 | 7/2006 | Seto et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0235387 A1 | 10/2006 | Peterman |
| 2006/0235532 A1 | 10/2006 | Meunier et al. |
| 2006/0241613 A1 | 10/2006 | Bruneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |

| | | |
|---|---|---|
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0043362 A1 | 2/2007 | Malandain et al. |
| 2007/0043363 A1 | 2/2007 | Malandain et al. |
| 2007/0100340 A1 | 5/2007 | Lange et al. |
| 2007/0112330 A1 | 5/2007 | Palasis |
| 2007/0123861 A1 | 5/2007 | Dewey et al. |
| 2007/0162000 A1 | 7/2007 | Perkins |
| 2007/0162136 A1 | 7/2007 | O'Neil et al. |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0198091 A1 | 8/2007 | Boyer et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276496 A1 | 11/2007 | Lange et al. |
| 2007/0276497 A1 | 11/2007 | Anderson |
| 2008/0021460 A1 | 1/2008 | Bruneau et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0195152 A1 | 8/2008 | Altarac et al. |
| 2008/0208341 A1 | 8/2008 | McCormack et al. |
| 2008/0215094 A1 | 9/2008 | Taylor |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105773 A1 | 4/2009 | Lange et al. |
| 2009/0240283 A1 | 9/2009 | Carls et al. |
| 2009/0326538 A1 | 12/2009 | Sennett et al. |
| 2010/0121379 A1 | 5/2010 | Edmond |
| 2010/0191241 A1 | 7/2010 | Mccormack et al. |
| 2010/0204732 A1 | 8/2010 | Aschmann et al. |
| 2010/0211101 A1 | 8/2010 | Blackwell et al. |
| 2010/0318190 A1 | 12/2010 | Collins et al. |

FOREIGN PATENT DOCUMENTS

| | | |
|---|---|---|
| EP | 0322334 B1 | 2/1992 |
| EP | 1138268 A1 | 10/2001 |
| EP | 1330987 A1 | 7/2003 |
| EP | 1854433 A1 | 11/2007 |
| EP | 1905392 A1 | 4/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 98/20939 | 5/1998 |
| WO | WO 99/59669 | 11/1999 |
| WO | WO 2004/047691 A1 | 6/2004 |
| WO | 2004/084743 A1 | 10/2004 |
| WO | WO 2004/084768 A2 | 10/2004 |
| WO | WO 2005/002474 A1 | 1/2005 |
| WO | WO 2005/009300 A1 | 2/2005 |
| WO | WO 2005/044118 A1 | 5/2005 |
| WO | WO 2005/110258 A1 | 11/2005 |
| WO | WO 2006/064356 A1 | 6/2006 |
| WO | WO 2007/034516 A1 | 3/2007 |
| WO | 2009/149079 A1 | 12/2009 |

OTHER PUBLICATIONS

"Tecnica Operatoria Per II Posizionarnento Della Protesi DIAM," date unknown, pp. 1-3.

"Wallis Operative Technique: Surgical Procedure for Treatment of Degenerative Disc Disease (DDD) of Lumbar Spine," date unknown, pp, 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol, 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp, S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Duff, "Methyl Methacrylate in Spinal Stabilization," Techniques in Spinal Fusion and Stabilization, Hitchon et al., eds., 1995, pp. 147-151, Ch. 14, Thieme, New York.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes Journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon at al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol, 6, No, 2.

Zdeblick et al., "Two-Point Fixation of the Lumbar Spine Differential Stability in Rotation," SPINE, 1991, pp. S298-S301, vol. 16, No. 6, Supplement.

Zucherman et al., "Clinical Efficacy of Spinal instrumentation in Lumbar Degenerative Disc Disease," SPINE, Jul. 1992, pp. 834-837, vol. 17, No. 7.

Anasetti et al., "Spine Stability After Implantation Of An Interspinous Device: An In Vitro And Finite Element Biomechanical Study," J. Neurosurg. Spine, Nov. 2010, vol. 13, pp. 568-575.

Bellini et al., "Biomechanics Of The Lumbar Spine After Dynamic Stabilization," J. Spinal Discord Tech., 2006, vol. 00, No. 00, pp. 1-7.

Buric et al., "DIAM Device For Low Back Pain In Degenerative Disc Disease 24 Months Follow-up," Advances in Minimally Invasive Surgery And Therapy For Spine And Nerves, Alexandre et al., eds., 2011, pp. 177-182, Spinger-Verlat/Wien.

Phillips et al., "Biomechanics of Posterior Dynamic Stabiling Device (DIAM) After Facetectomy And Disectomy," The Spine Journal, 2006, vol. 6, pp. 714-722.

Taylor et al., "Device for Intervertebral Assisted Motion: Technique And Intial Results," 22 Neurosurg. Focus, Jan. 2007, vol. 22, No. 1, pp. 1-6.

Wilke et al., "Biomedical Effect Of Different Lumbar Interspinous Implants On Flexibilty And Intradiscal Pressure," Eur Spine J., Vo. 17, published online Jun. 27, 2008, pp. 1049-1056.

Zhao et al., "Efficacy Of The Dynamic Interspinous Assisted Motion System In Clinical Treatment Of Degenerative Lumbar Disease," Chin. Med. J., 2010, vol. 123, No. 21, pp. 2974-2977.

* cited by examiner

MULTI-CHAMBER EXPANDABLE INTERSPINOUS PROCESS SPACER

This application is a divisional of prior application Ser. No. 11/413,587, filed 28 Apr. 2006, which is incorporated herein in its entirety by reference.

FIELD OF THE DISCLOSURE

The present disclosure relates generally to orthopedics and orthopedic surgery. More specifically, the present disclosure relates to devices used to support adjacent spinous processes.

BACKGROUND

In human anatomy, the spine is a generally flexible column that can take tensile and compressive loads. The spine also allows bending motion and provides a place of attachment for keels, muscles and ligaments. Generally, the spine is divided into three sections: the cervical spine, the thoracic spine and the lumbar spine. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending, or flexure, of the spine. Thus, the intervertebral discs are under constant muscular and/or gravitational pressure and generally, the intervertebral discs are the first parts of the' lumbar spine to show signs of deterioration.

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

DETAILED DESCRIPTION OF THE DRAWINGS

A multi-chamber expandable interspinous process spacer or brace is disclosed and can include at least two chambers. Each of the at least two chambers can receive an injectable biocompatible material. Further, the multi-chamber expandable interspinous process brace can be moved between a deflated configuration and an inflated configuration. In the inflated configuration, the multi-chamber expandable interspinous process brace can engage and support a superior spinous process and an inferior spinous process.

In another embodiment, a method of treating a spine is disclosed and can include installing a multi-chamber expandable interspinous process brace between a superior spinous process and an inferior spinous process. The method can also include inflating at least two chambers within the multi-chamber expandable interspinous process brace to support the superior spinous process and the inferior spinous process.

In still another embodiment, a method of treating a spine is disclosed and can include distracting a superior spinous process and an inferior spinous process. Also, the method can include installing a multi-chamber expandable interspinous process brace between a superior spinous process and an inferior spinous process. Moreover, the method can include inflating at least two chambers within the multi-chamber expandable interspinous process brace to support the superior spinous process and the inferior spinous process.

In yet another embodiment, a kit for field use is disclosed and can include a multi-chamber expandable interspinous process brace that can have at least two chambers configured to receive an injectable biocompatible material. The kit can also include an injectable biocompatible material.

In still yet another embodiment, a kit for field use is disclosed and can include a multi-chamber expandable interspinous process brace that can include at least two chambers configured to receive an injectable biocompatible material. Additionally, the kit can include an injectable biocompatible material and a tether that can circumscribe the multi-chamber expandable interspinous process brace, a superior spinous process, and an inferior spinous process.

Description of Relevant Anatomy

Figure 1:
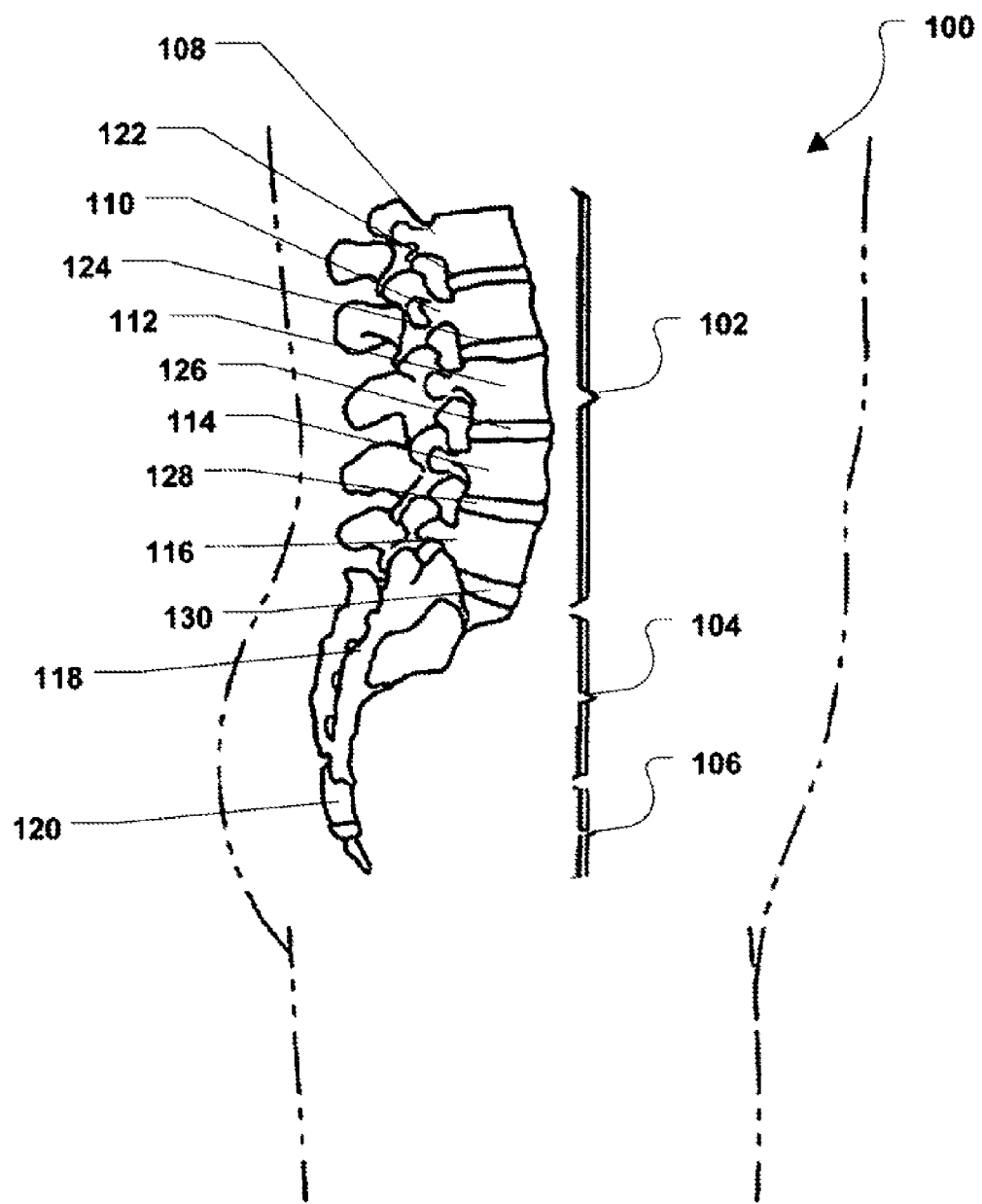
FIG. 1 is a lateral view of a portion of a vertebral column.

Referring initially to FIG. 1, a portion of a vertebral column, designated 100, is shown. As depicted, the vertebral column 100 includes a lumbar region 102, a sacral region 104, and a coccygeal region 106. As is known in the art, the vertebral column 100 also includes a cervical region and a thoracic region. For clarity and ease of discussion, the cervical region and the thoracic region are not illustrated.

As shown in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, damaged, or otherwise in need of repair, treatment of that intervertebral lumbar disc 122, 124, 126, 128, 130 can be effected in accordance with one or more of the embodiments described herein.

Figure 2:
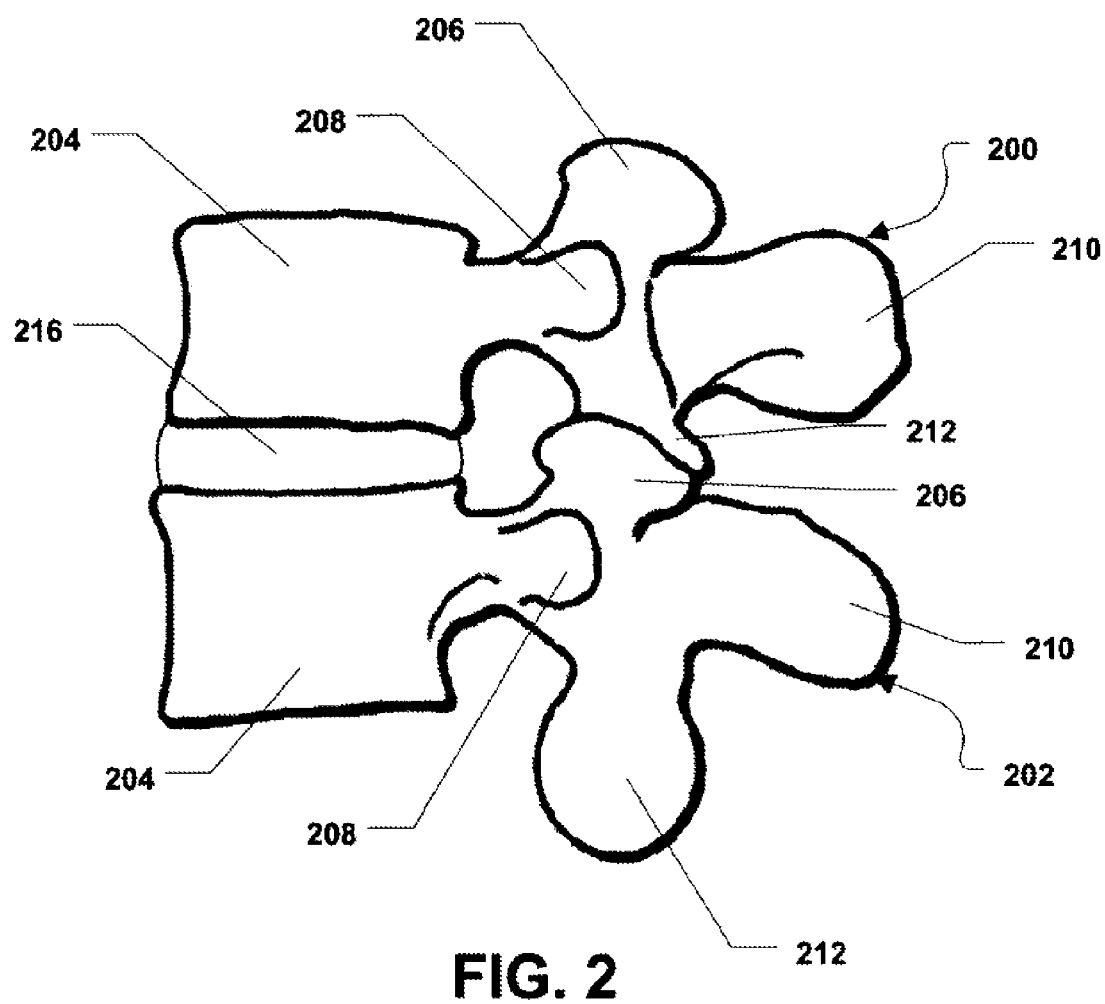
FIG. 2 is a lateral view of a pair of adjacent vertebrae.

FIG. 2 depicts a detailed lateral view of two adjacent vertebrae, e.g., two of the lumbar vertebra 108, 110, 112, 114, 116 shown in FIG. 1. FIG. 2 illustrates a superior vertebra 200 and an inferior vertebra 202. As shown, each vertebra 200, 202 includes a vertebral body 204, a superior articular process 206, a transverse process 208, a spinous process 210 and an inferior articular process 212. FIG. 2 further depicts an intervertebral disc 216 between the superior vertebra 200 and the inferior vertebra 202.

Figure 3:
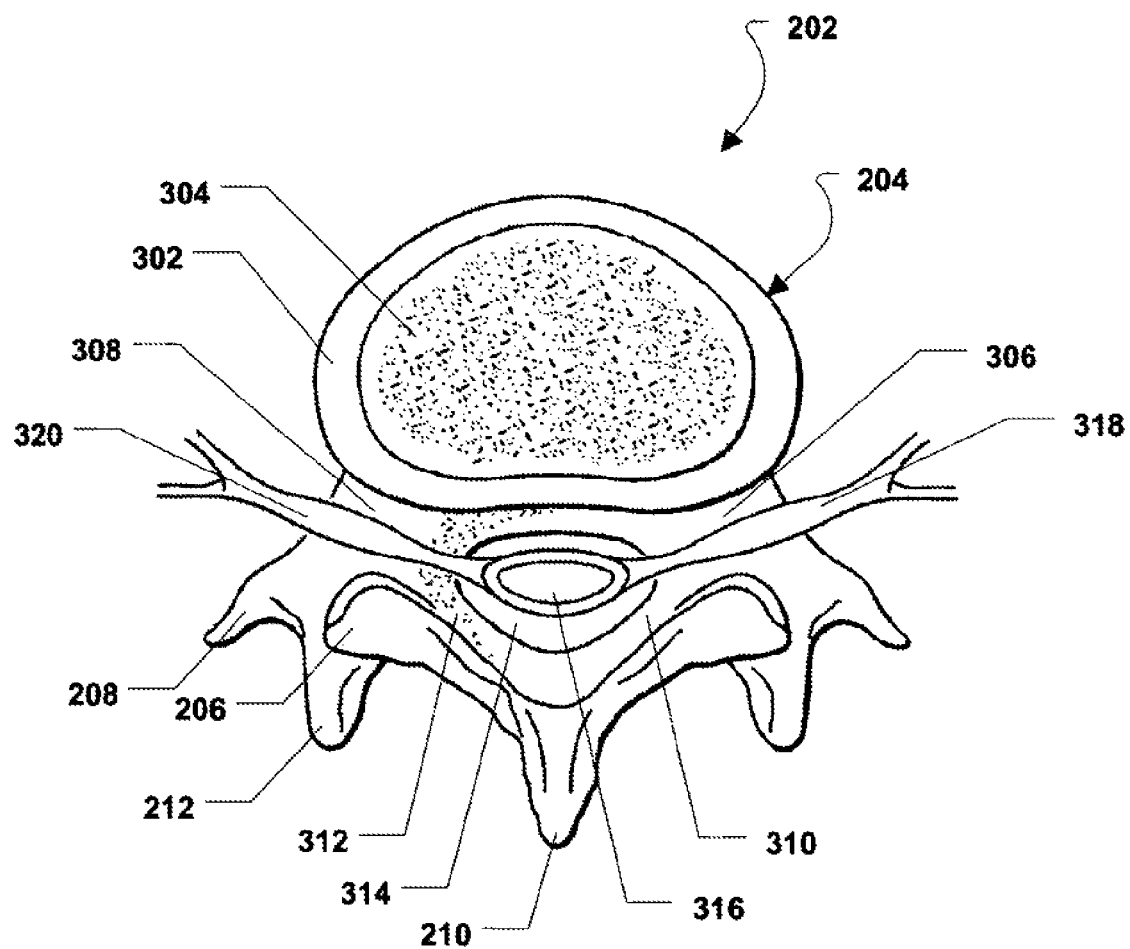
FIG. 3 is a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

It is well known in the art that the vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Figure 4:
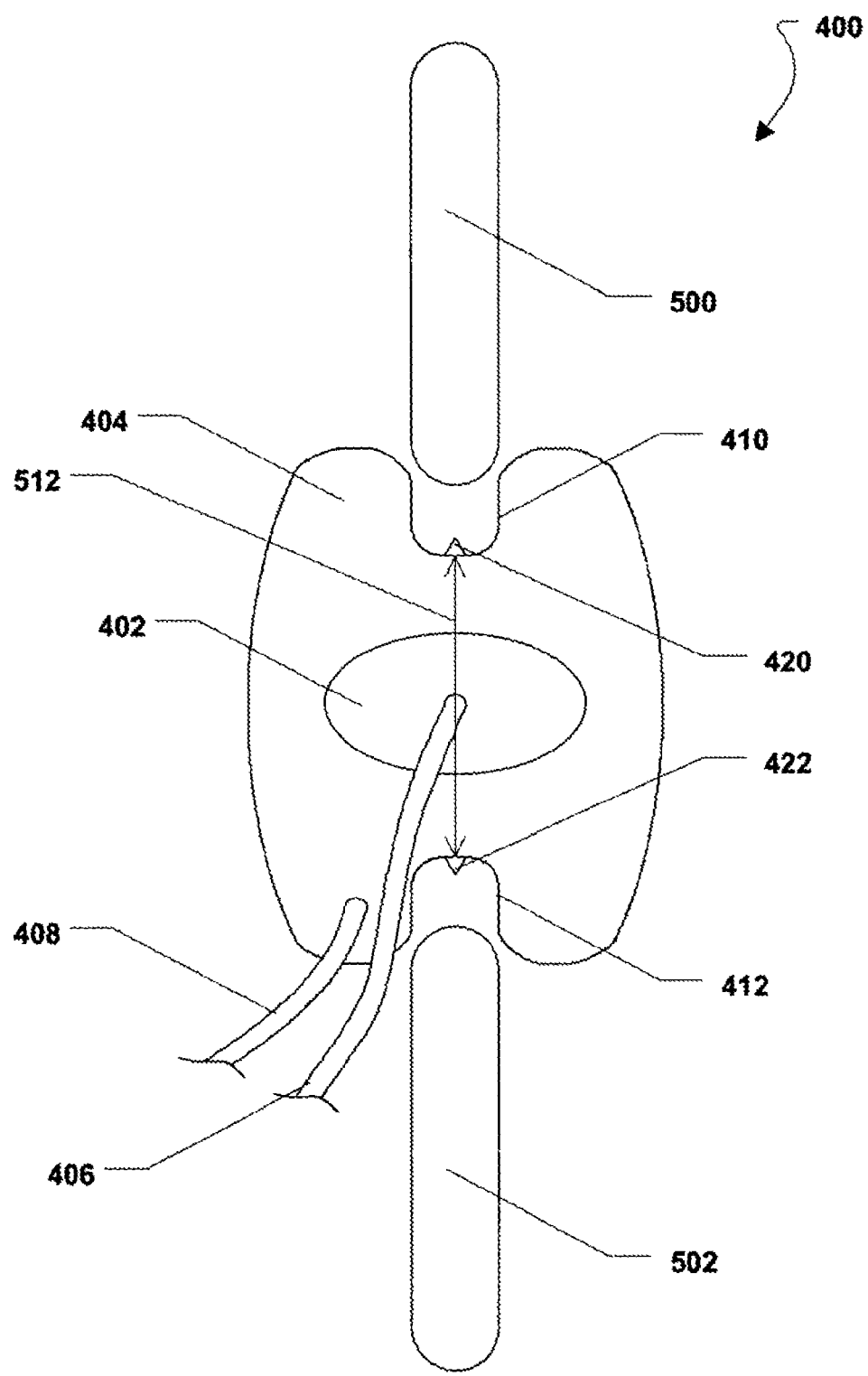
FIG. 4 is a plan view of a first multi-chamber expandable interspinous process spacer in a deflated configuration.
Figure 5:
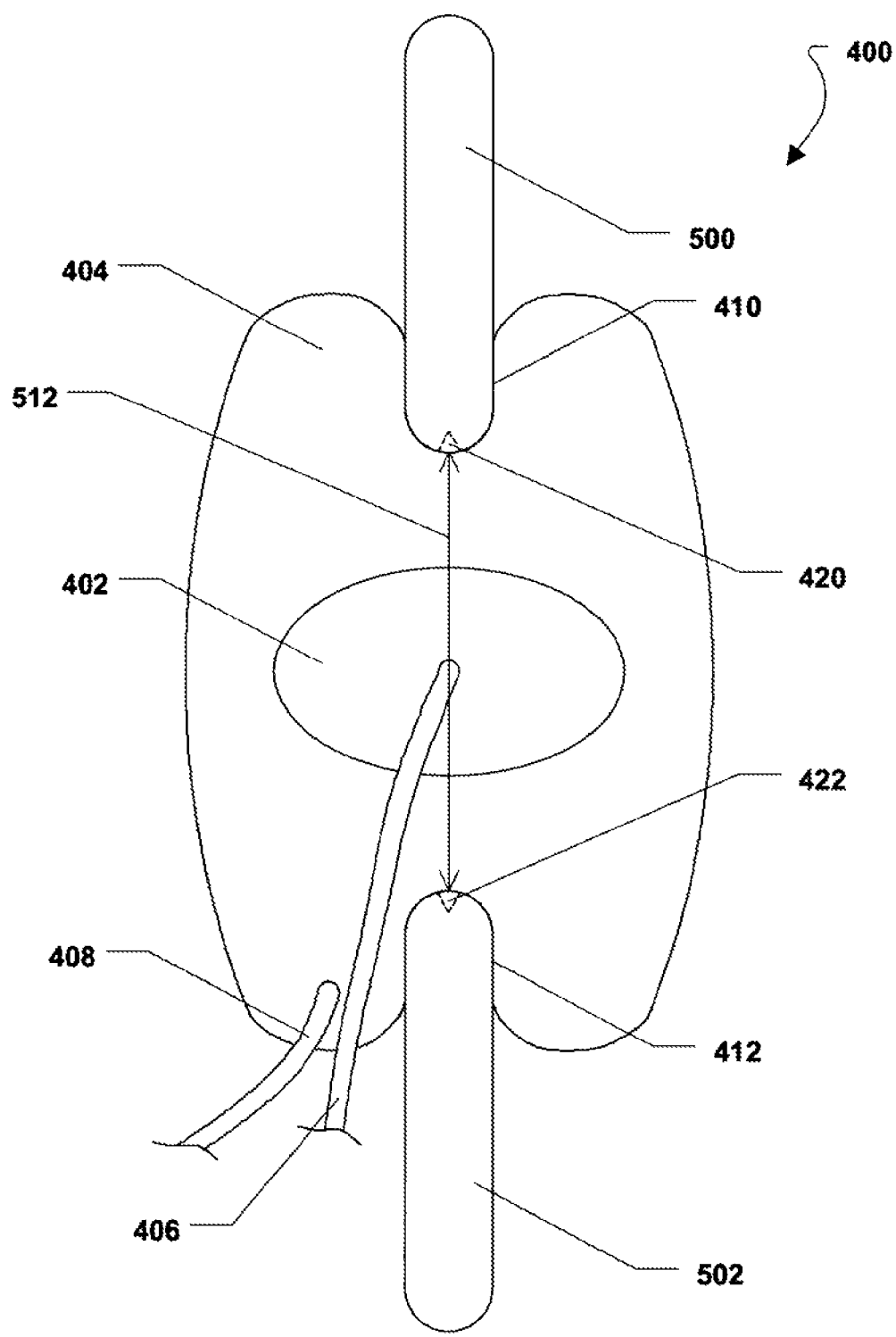
FIG. 5 is a plan view of the first multi-chamber expandable interspinous process spacer in an inflated configuration.
Figure 6:
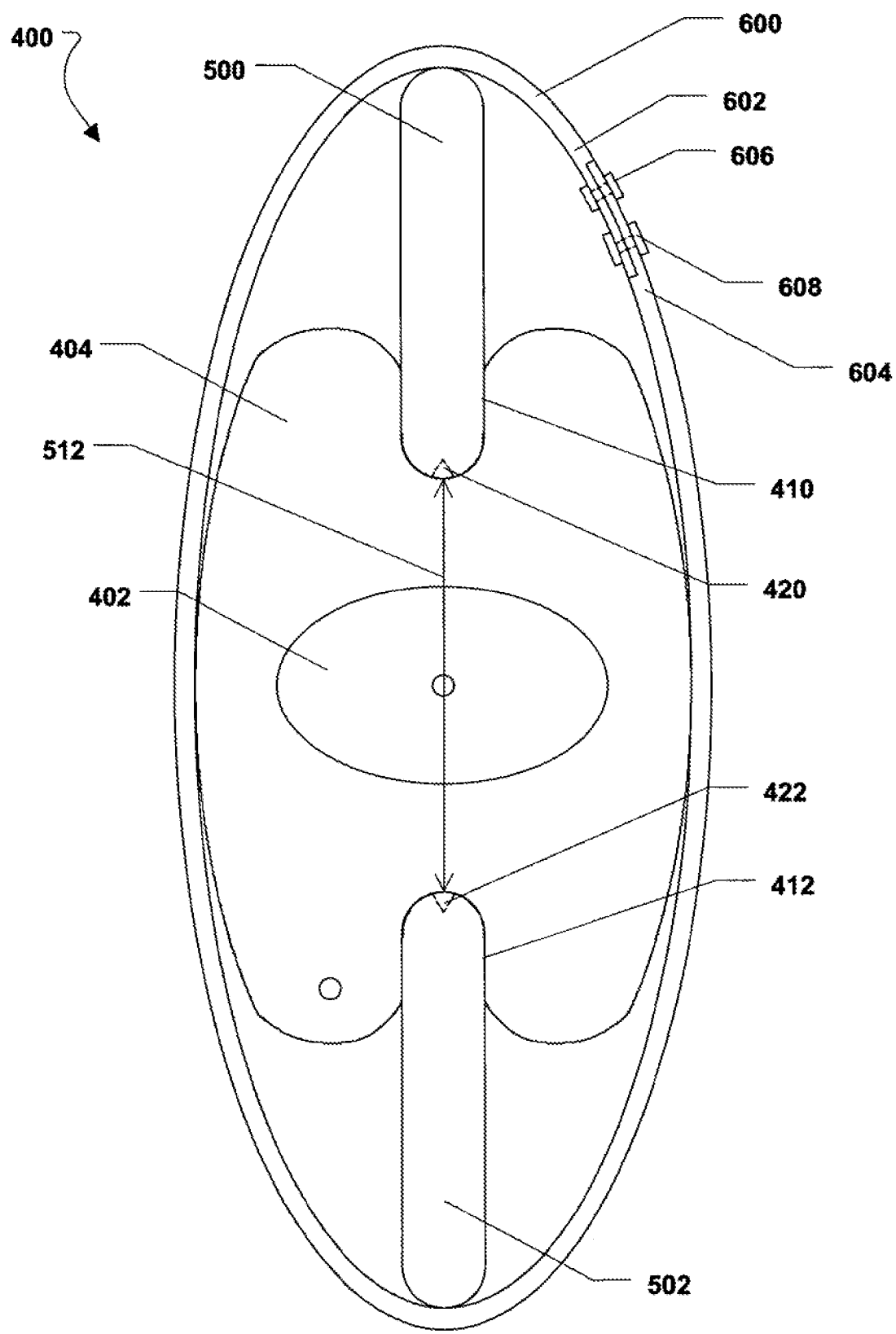
FIG. 6 is a plan view of the first multi-chamber expandable interspinous process spacer in an inflated configuration with a tether installed there around.

Description of a First Embodiment of a Multi-Chamber Expandable Interspinous Process Brace Referring to FIG. 4 through FIG. 6, a first embodiment of a multi-chamber expandable interspinous process brace is shown and is generally designated 400. As shown, the multi-chamber expandable interspinous process brace 400 includes an interior chamber 402 and an exterior chamber 404.

In a particular embodiment, the interior chamber 402 can be generally elliptical. Alternatively, the interior chamber 402 can be generally spherical, generally pyramidal, generally conical, generally frustal, generally cubic, generally polyhedral, or a combination thereof. The exterior chamber 404 can be provided in a shape that can generally engage and/or stabilize at least one spinous process, such as, for example, the spinous processes of two adjacent vertebrae. In a particular embodiment, the exterior chamber 404 can be generally H-shaped.

Further, in a particular embodiment, the chambers 402, 404 can be made from one or more expandable biocompatible materials. For example, the materials can be silicones, polyurethanes, polycarbonate urethanes, polyethylene terephthalate, silicone copolymers, polyolefins, or any combination thereof. Also, the chambers 402, 404 can be non-porous or micro-porous, e.g., for venting purposes.

As shown in FIG. 4, the interior chamber 402 can include a first injection tube 406. Further, the exterior chamber 404 can include a second injection tube 408. The injection tubes 406, 408 can be used to provide an injectable biocompatible material to the chambers 402, 404. In a particular embodiment, each of the interior chamber 402 and the exterior chamber 404 of the multi-chamber expandable interspinous process brace 400 can be expanded from a respective deflated configuration, shown in FIG. 4, to one of a plurality of inflated configurations, shown in FIG. 5, up to a maximum inflated configuration. Further, after the interior chamber 402 and the exterior chamber 404 are inflated, or otherwise expanded, the injection tubes 406, 408 can be removed, as depicted in FIG. 6.

In a particular embodiment, the multi-chamber expandable interspinous process brace 400 can include a first self-sealing valve (not shown) within the interior chamber 402, e.g., adjacent to the first injection tube 406. Moreover, the multi-chamber expandable interspinous process brace 400 can include a second self-sealing valve (not shown) within the exterior chamber 404, e.g., adjacent to the second injection tube 408. The self-sealing valves can prevent the chambers 402, 404 from leaking material after the chambers 402, 404 are inflated and the injection tubes 406, 408 are removed.

As illustrated in FIG. 4 through FIG. 6, the exterior chamber 404 can include a superior spinous process pocket 410 and an inferior spinous process pocket 412. Further, a superior spinous process engagement structure 420 can extend from the exterior chamber 404 within the superior spinous process pocket 410. Also, an inferior spinous process engagement structure 422 can extend from the exterior chamber 404 within the inferior spinous process pocket 412. In a particular embodiment, each of the spinous process engagement structures 420, 422 can be one or more spikes, one or more teeth, a combination thereof, or some other structure configured to engage a spinous process.

FIG. 4 through FIG. 6 indicate that the multi-chamber expandable interspinous process brace 400 can be implanted between a superior spinous process 500 and an inferior spinous process 502. In a particular embodiment, the chambers 402, 404 can be inflated so the exterior chamber 404 engages the spinous processes 500, 502. In a particular embodiment, when the multi-chamber expandable interspinous process brace 400 is properly installed and inflated between the superior spinous process 500 and the inferior spinous process 502, the superior spinous process pocket 410 can engage and support the superior spinous process 500. Further, the inferior spinous process pocket 412 can engage and support an inferior spinous process 502.

More specifically, the superior spinous process engagement structure 420 can extend slightly into and engage the superior spinous process 500. Also, the inferior spinous process engagement structure 422 can extend slightly into and engage the inferior spinous process 502. Accordingly, the spinous process engagement structures 420, 422, the spinous process pockets 410, 412, or a combination thereof can substantially prevent the multi-chamber expandable interspinous process brace 400 from migrating with respect to the spinous processes 500, 502.

Also, in a particular embodiment, the multi-chamber expandable interspinous process brace 400 can be movable between a deflated configuration, shown in FIG. 4, and one or more inflated configurations, shown in FIG. 5 and FIG. 6. In the deflated configuration, a distance 512 between the superior spinous process pocket 410 and the inferior spinous process pocket 412 can be at a minimum. However, as one or more materials are injected into the chambers 402, 404, the distance 512 between the superior spinous process pocket 410 and the inferior spinous process pocket 412 can increase.

Accordingly, the multi-chamber expandable interspinous process brace 400 can be installed between a superior spinous process 500 and an inferior spinous process 502. Further, the multi-chamber expandable interspinous process brace 400 can be expanded, e.g., by injecting one or more materials into the chambers 402, 404, in order to increase the distance between the superior spinous process 500 and the inferior spinous process 502.

Alternatively, a distractor can be used to increase the distance between the superior spinous process 500 and the inferior spinous process 502 and the multi-chamber expandable interspinous process brace 400 can be expanded to support the superior spinous process 500 and the inferior spinous process 502. After the multi-chamber expandable interspinous process brace 400 is expanded accordingly, the distractor can be removed and the multi-chamber expandable interspinous process brace 400 can support the superior spinous process 500 and the inferior spinous process 502 to substantially prevent the distance between the superior spinous process 502 and the inferior spinous process 500 from returning to a pre-distraction value.

In a particular embodiment, the multi-chamber expandable interspinous process brace 400 can be injected with one or more injectable biocompatible materials that remain elastic after curing. Further, the injectable biocompatible materials can include polymer materials that remain elastic after curing. Also, the injectable biocompatible materials can include ceramics.

For example, the polymer materials can include polyurethanes, polyolefins, silicones, silicone polyurethane copolymers, polymethylmethacrylate (PMMA), epoxies, cyanoacrylate, hydrogels, or a combination thereof. Further, the polyolefin materials can include polypropylenes, polyethylenes, halogenated polyolefins, or flouropolyolefins.

The hydrogels can include polyacrylamide (PAAM), poly-N-isopropylacrylamine (PNIPAM), polyvinyl methylether (PVM), polyvinyl alcohol (PVA), polyethyl hydroxyethyl cellulose, poly (2-ethyl) oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or a combination thereof.

In a particular embodiment, the ceramics can include calcium phosphate, hydroxyapatite, calcium sulfate, bioactive glass, or a combination thereof. In an alternative embodiment, the injectable biocompatible materials can include one or more fluids such as sterile water, saline, or sterile air.

In a particular embodiment, the hardness of the material used to inflate the interior chamber 402 can be less than or equal to the hardness of the material used to inflate the exterior chamber 404, i.e., after the materials used to inflate the interior chamber 402 and the exterior chamber 404 are cured. Alternatively, the viscosity of the material used to inflate the interior chamber 402 can be less than or equal to the viscosity of the material used to inflate the exterior chamber 404. In a particular embodiment, certain or all of the injected materials can be cured or cross-linked in situ to form a solid interspinous process brace with non-uniform bulk properties.

FIG. 6 indicates that a tether 600 can be installed around the multi-chamber expandable interspinous process brace 400, after the multi-chamber expandable interspinous process brace 400 is expanded as described herein. As shown, the tether 600 can include a proximal end 602 and a distal end 604. In a particular embodiment, the tether 600 can circumscribe the multi-chamber expandable interspinous process brace 400 and the spinous processes 500, 502. Further, the ends 602, 604 of the tether 600 can be brought together and one or more fasteners can be installed therethrough to connect the ends 602, 604. Accordingly, the tether 600 can be installed in order to prevent the distance between the spinous processes 500, 502 from substantially increasing beyond the distance provided by the multi-chamber expandable interspinous process brace 400 after it is expanded and to maintain engagement of the interspinous processes with the spinous process pockets 410, 412, the engagement structures 420, 422, or a combination thereof.

In a particular embodiment, the tether 600 can comprise a biocompatible elastomeric material that flexes during installation and provides a resistance fit against the inferior process. Further, the tether 600 can comprise a substantially non-resorbable suture or the like.

Figure 7:
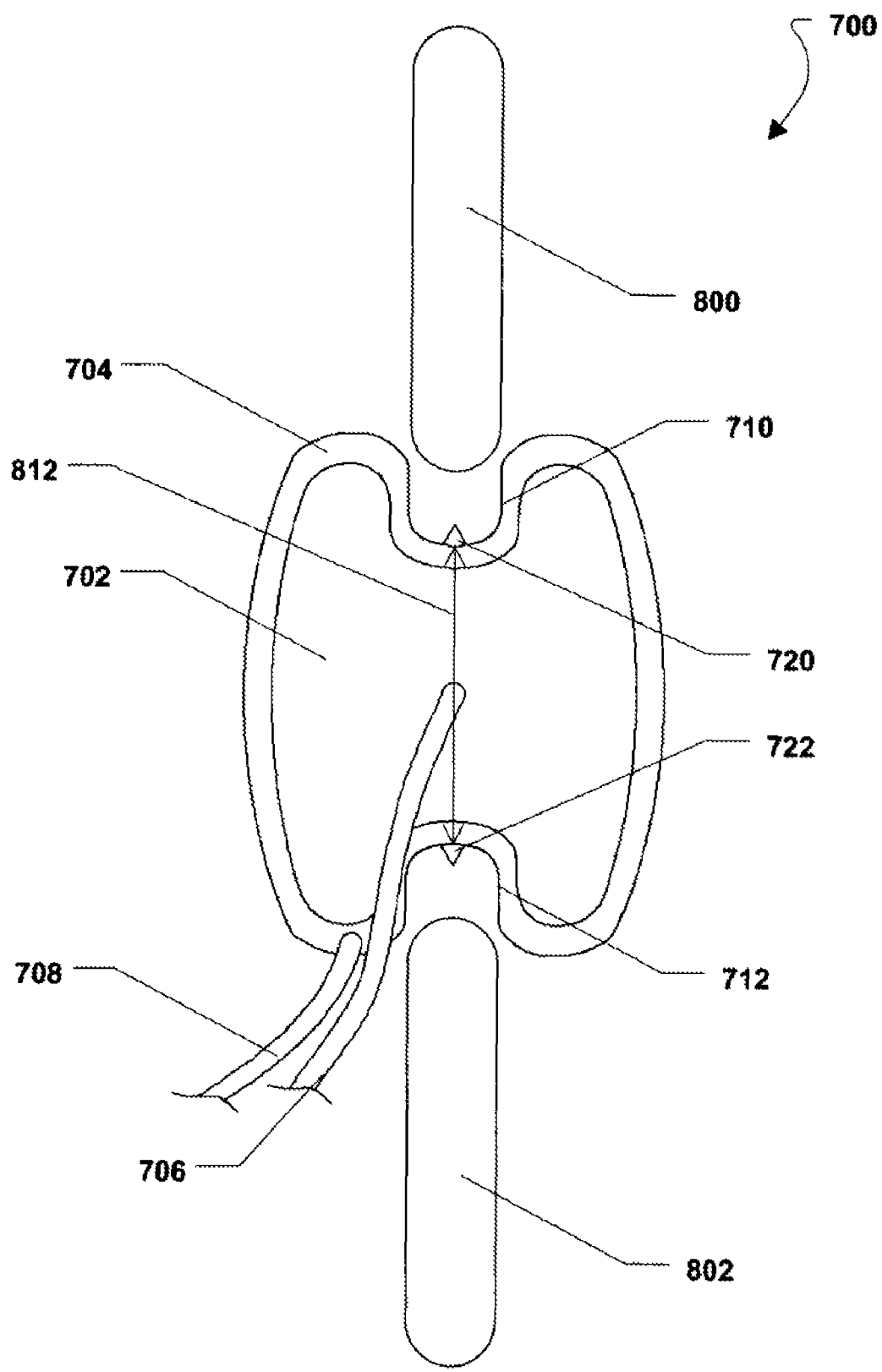
FIG. 7 is a plan view of a second multi-chamber expandable interspinous process spacer in a deflated configuration.
Figure 8:
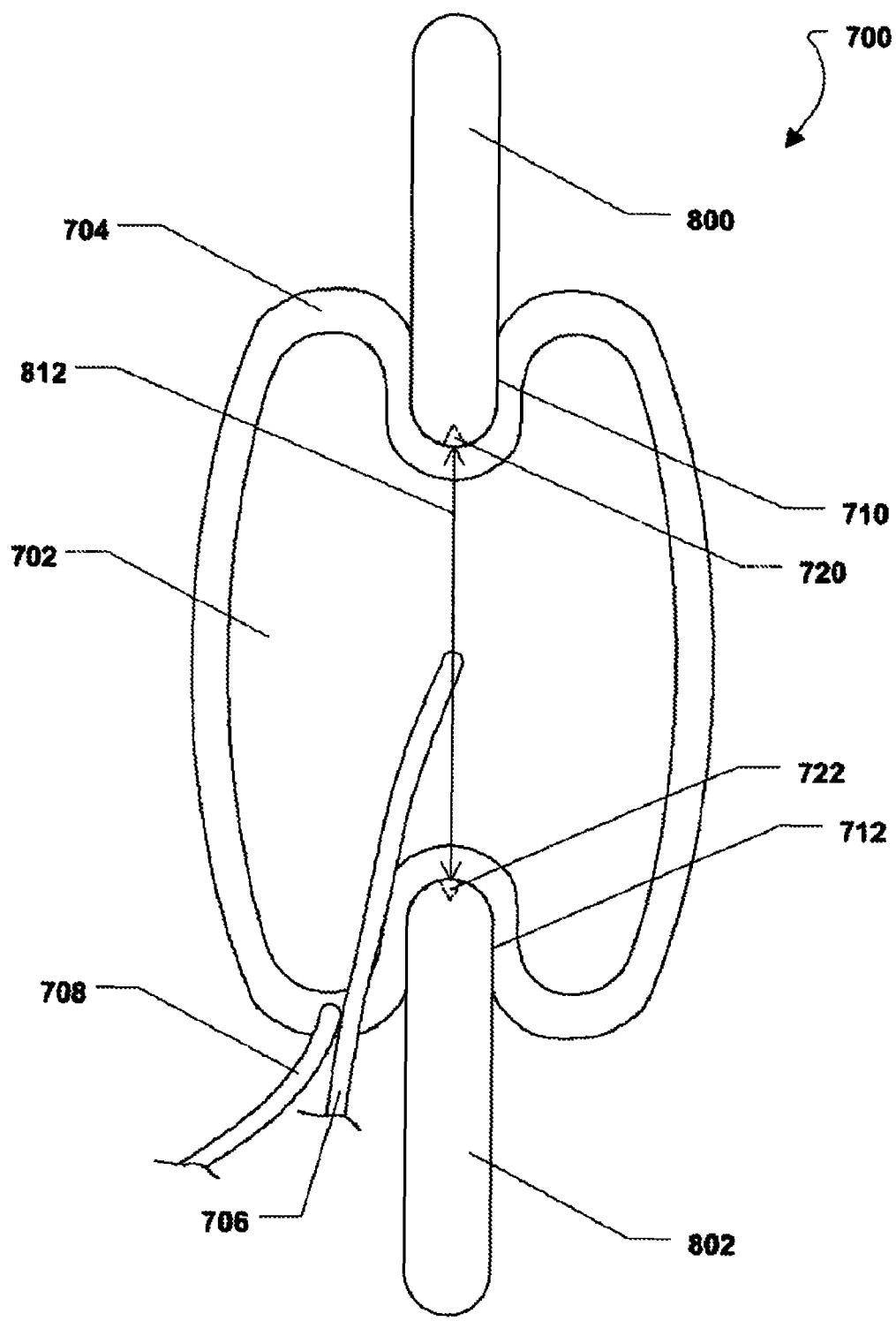
FIG. 8 is a plan view of the second multi-chamber expandable interspinous process spacer in an inflated configuration.
Figure 9:
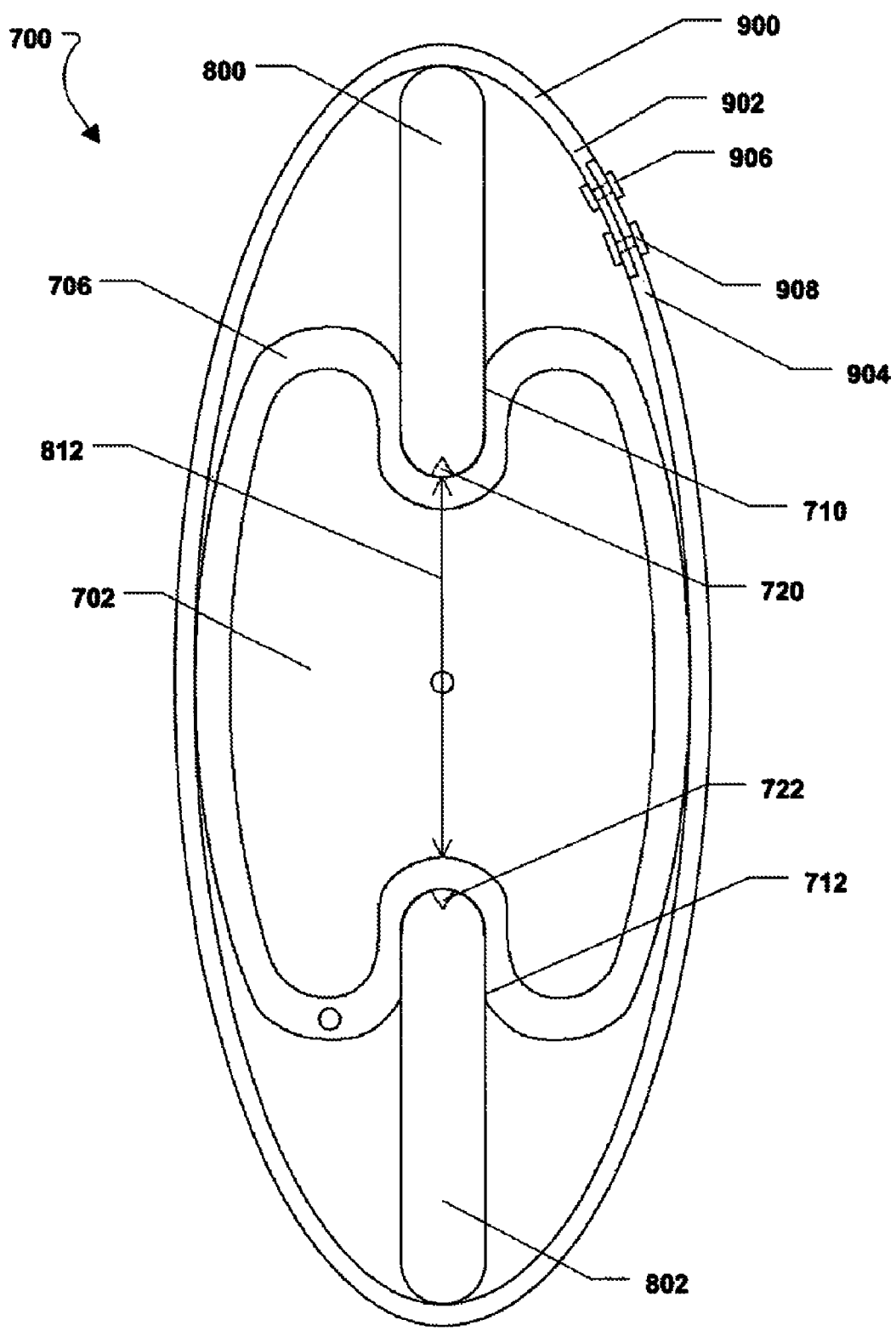
FIG. 9 is a plan view of the second multi-chamber expandable interspinous process spacer in an inflated configuration with a tether installed there around.

Description of a Second Embodiment of a
Multi-Chamber Expandable Interspinous Process
Brace Referring to FIG. 7 through FIG. 9, a second embodiment of a multi-chamber expandable interspinous process brace is shown and is generally designated 700. As shown, the multi-chamber expandable interspinous process brace 700 includes an interior chamber 702 and an exterior chamber 704.

The interior chamber 702 and the exterior chamber 704 can be provided in a shape that can generally engage and/or stabilize at least one spinous process, such as, for example, the spinous processes of two adjacent vertebrae. In a particular embodiment, the interior chamber 702 can be generally H-shaped. Also, in a particular embodiment, the exterior chamber 704 can be hollow and generally H-shaped. More specifically, the exterior chamber 704 can be shaped to match the outer perimeter of the interior chamber 702.

Further, in a particular embodiment, the chambers 702, 704 can be made from one or more expandable biocompatible materials. For example, the materials can be silicones, polyurethanes, polycarbonate urethanes, polyethylene terephthalate, silicone copolymers, polyolefins, or any combination thereof. Also, the chambers 702, 704 can be non-porous or micro-porous, e.g., for venting purposes.

As shown in FIG. 7, the interior chamber 702 can include a first injection tube 706. Further, the exterior chamber 704 can include a second injection tube 708. The injection tubes 706, 708 can be used to provide an injectable biocompatible material to the chambers 702, 704. In a particular embodiment, each of the interior chamber 702 and the exterior chamber 704 of the multi-chamber expandable interspinous process brace 700 can be expanded from a respective deflated configuration, shown in FIG. 7, to one of a plurality of inflated configurations, shown in FIG. 8, up to a maximum inflated configuration. Further, after the interior chamber 702 and the exterior chamber 704 are inflated, or otherwise expanded, the injection tubes 706, 708 can be removed, as depicted in FIG. 9.

In a particular embodiment, the multi-chamber expandable interspinous process brace 700 can include a first self-sealing valve (not shown) within the interior chamber 702, e.g., adjacent to the first injection tube 706. Moreover, the multi-chamber expandable interspinous process brace 700 can include a second self-sealing valve (not shown) within the exterior chamber 704, e.g., adjacent to the second injection tube 708. The self-sealing valves can prevent the chambers 702, 704 from leaking material after the chambers 702, 704 are inflated and the injection tubes 706, 708 are removed.

As illustrated in FIG. 7 through FIG. 9, the exterior chamber 704 can include a superior spinous process pocket 710 and an inferior spinous process pocket 712. Further, a superior spinous process engagement structure 720 can extend from the exterior chamber 704 within the superior spinous process pocket 710. Also, an inferior spinous process engagement structure 722 can extend from the exterior chamber 704 within the inferior spinous process pocket 712. In a particular embodiment, each of the spinous process engagement structures 720, 722 can be one or more spikes, one or more teeth, a combination thereof, or some other structure configured to engage a spinous process.

FIG. 7 through FIG. 9 indicate that the multi-chamber expandable interspinous process brace 700 can be implanted between a superior spinous process 800 and an inferior spinous process 802. In a particular embodiment, the chambers 702, 704 can be inflated so the exterior chamber 704 engages the spinous processes 800, 802. In a particular embodiment, when the multi-chamber expandable interspinous process brace 700 is properly installed and inflated between the superior spinous process 800 and the inferior spinous process 802, the superior spinous process pocket 710 can engage and support the superior spinous process 800. Further, the inferior spinous process pocket 712 can engage and support an inferior spinous process 802.

More specifically, the superior spinous process engagement structure 720 can extend slightly into and engage the superior spinous process 800. Also, the inferior spinous process engagement structure 722 can extend slightly into and engage the inferior spinous process 802. Accordingly, the spinous process engagement structures 720, 722, the spinous process pockets 710, 712, or a combination thereof can substantially prevent the multi-chamber expandable interspinous process brace 700 from migrating with respect to the spinous processes 800, 802.

Also, in a particular embodiment, the multi-chamber expandable interspinous process brace 700 can be movable between a deflated configuration, shown in FIG. 7, and one or more inflated configurations, shown in FIG. 8 and FIG. 9. In the deflated configuration, a distance 812 between the superior spinous process pocket 710 and the inferior spinous process pocket 712 can be at a minimum. However, as one or more materials are injected into the chambers 702, 704, the distance 812 between the superior spinous process pocket 710 and the inferior spinous process pocket 712 can increase.

Accordingly, the multi-chamber expandable interspinous process brace 700 can be installed between a superior spinous process 800 and an inferior spinous process 802. Further, the multi-chamber expandable interspinous process brace 700 can be expanded, e.g., by injecting one or more materials into the chambers 702, 704, in order to increase the distance between the superior spinous process 800 and the inferior spinous process 802.

Alternatively, a distractor can be used to increase the distance between the superior spinous process 800 and the inferior spinous process 802 and the multi-chamber expandable interspinous process brace 700 can be expanded to support the superior spinous process 800 and the inferior spinous process 802. After the multi-chamber expandable interspinous process brace 700 is expanded accordingly, the distractor can be removed and the multi-chamber expandable interspinous process brace 700 can support the superior spinous process 800 and the inferior spinous process 802 to substantially prevent the distance between the superior spinous process 802 and the inferior spinous process 800 from returning to a pre-distraction value.

In a particular embodiment, the multi-chamber expandable interspinous process brace 700 can be injected with one or more injectable biocompatible materials that remain elastic after curing. Further, the injectable biocompatible materials can include polymer materials that remain elastic after curing. Also, the injectable biocompatible materials can include ceramics.

For example, the polymer materials can include polyurethanes, polyolefins, silicones, silicone polyurethane copolymers, polymethylmethacrylate (PMMA), epoxies, cyanoacrylates, hydrogels, or a combination thereof. Further, the polyolefin materials can include polypropylenes, polyethylenes, halogenated polyolefins, or flouropolyolefins.

The hydrogels can include polyacrylamide (PAAM), poly-N-isopropylacrylamine (PNIPAM), polyvinyl methylether (PVM), polyvinyl alcohol (PVA), polyethyl hydroxyethyl cellulose, poly (2-ethyl) oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or a combination thereof.

In a particular embodiment, the ceramics can include calcium phosphate, hydroxyapatite, calcium sulfate, bioactive glass, or a combination thereof. In an alternative embodiment, the injectable biocompatible materials can include one or more fluids such as sterile water, saline, or sterile air.

In a particular embodiment, the hardness of the material used to inflate the interior chamber 702 can be greater than or equal to the hardness of the material used to inflate the exterior chamber 704, i.e., after the materials used to inflate the interior chamber 702 and the exterior chamber 704 are cured. Alternatively, the viscosity of the material used to inflate the interior chamber 702 can be greater than or equal to the viscosity of the material used to inflate the exterior chamber 704. In a particular embodiment, certain or all of the injected materials can be cured or cross-linked in situ to form a solid interspinous process brace with non-uniform bulk properties.

FIG. 9 indicates that a tether 900 can be installed around the multi-chamber expandable interspinous process brace 700, after the multi-chamber expandable interspinous process brace 700 is expanded as described herein. As shown, the tether 900 can include a proximal end 902 and a distal end 904. In a particular embodiment, the tether 900 can circumscribe the multi-chamber expandable interspinous process brace 700 and the spinous processes 800, 802. Further, the ends 902, 904 of the tether 900 can be brought together and one or more fasteners can be installed therethrough to connect the ends 902, 904. Accordingly, the tether 900 can be installed in order to prevent the distance between the spinous processes 800, 802 from substantially increasing beyond the distance provided by the multi-chamber expandable interspinous process brace 700 after it is expanded and to maintain engagement of the interspinous processes with the spinous process pockets 710, 712, the engagement structures 720, 722, or a combination thereof.

In a particular embodiment, the tether 900 can comprise a biocompatible elastomeric material that flexes during installation and provides a resistance fit against the inferior process. Further, the tether 900 can comprise a substantially non-resorbable suture or the like.

Figure 10:
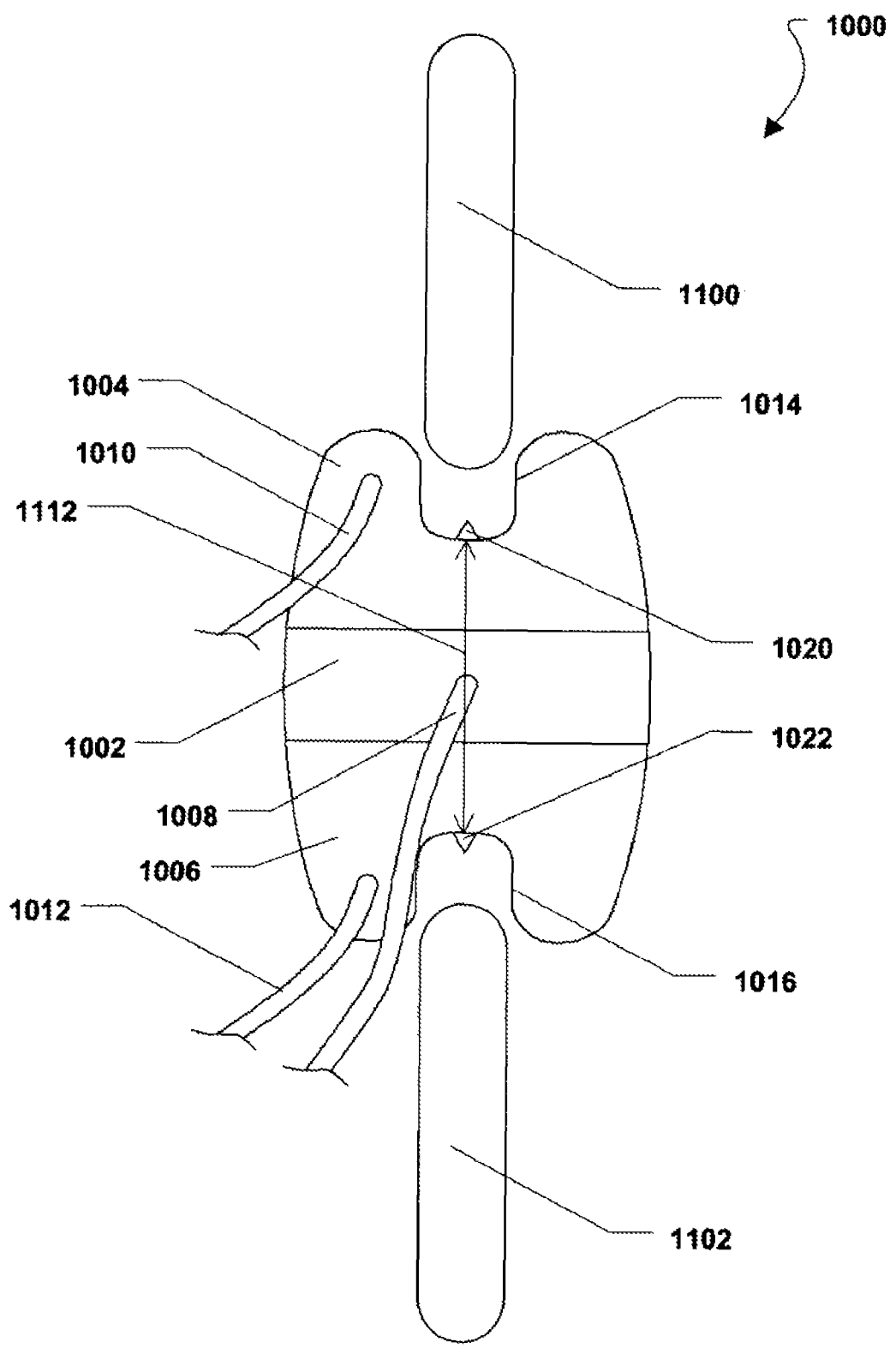
FIG. 10 is a plan view of a third multi-chamber expandable interspinous process spacer in a deflated configuration.
Figure 11:
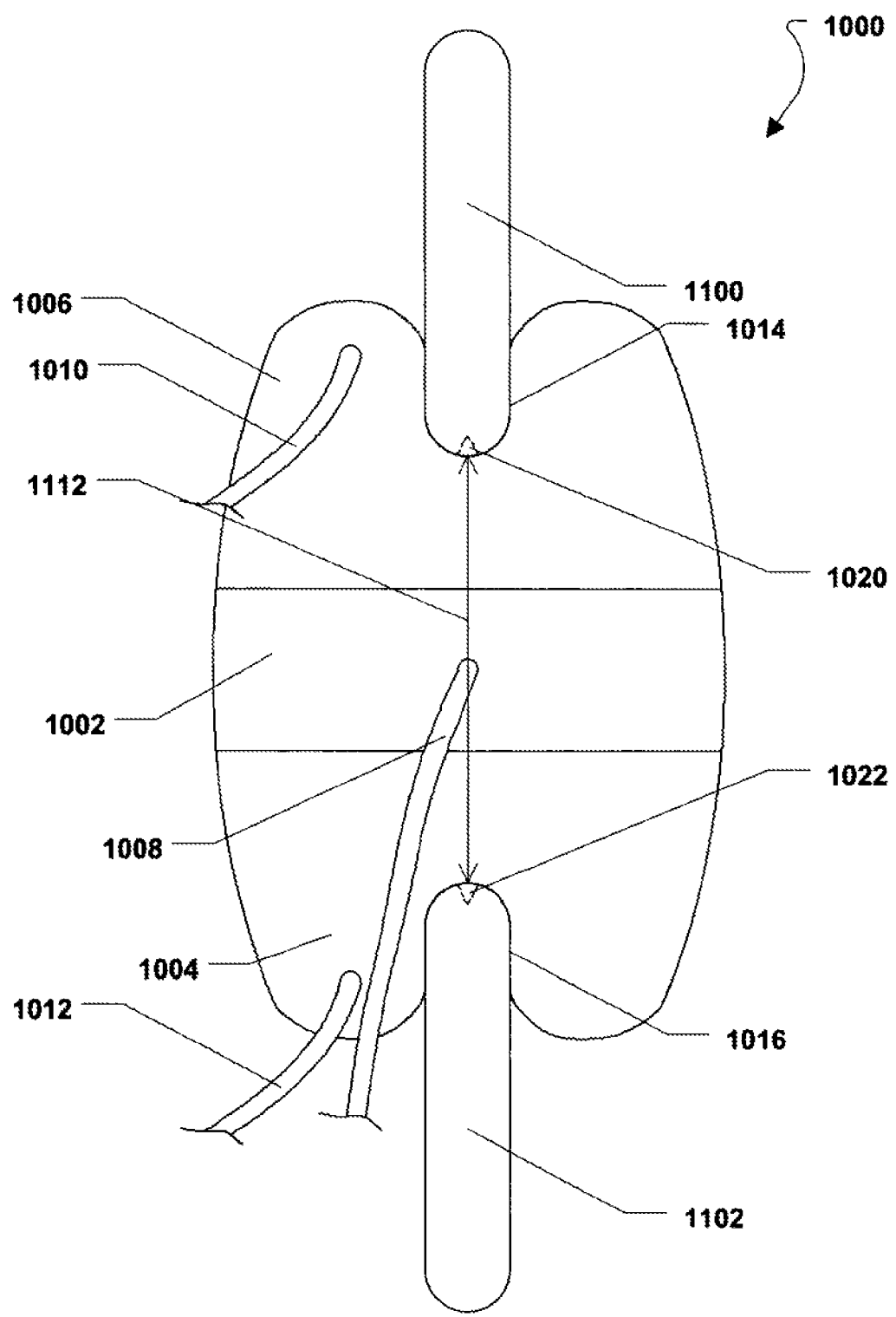
FIG. 11 is a plan view of the third multi-chamber expandable interspinous process spacer in an inflated configuration.
Figure 12:
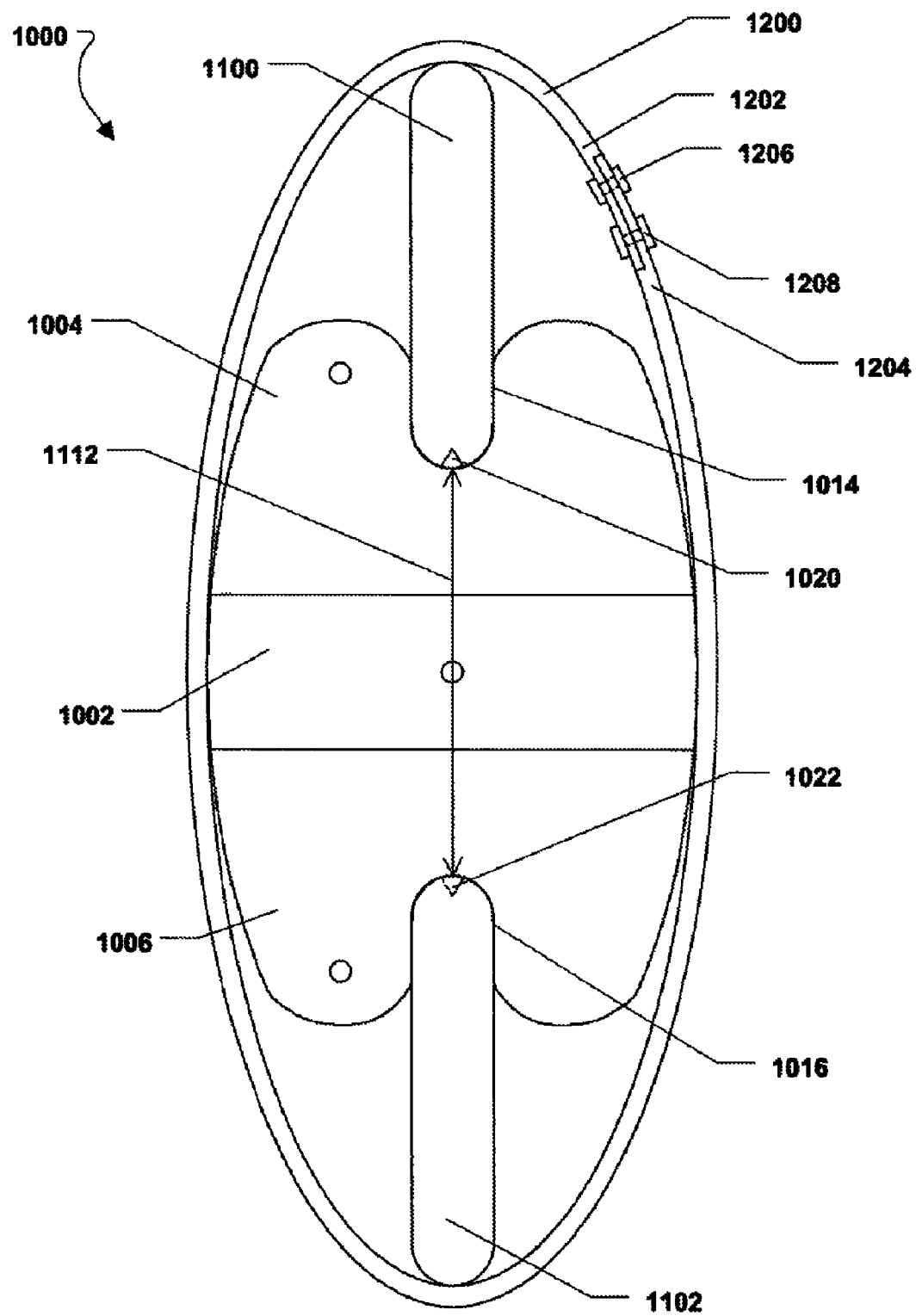
FIG. 12 is a plan view of the third multi-chamber expandable interspinous process spacer in an inflated configuration with a tether installed there around.

Description of a Third Embodiment of a Multi-Chamber Expandable Interspinous Process Brace Referring to FIG. 10 through FIG. 12, a third embodiment of a multi-chamber expandable interspinous process brace is shown and is generally designated 1000. As shown, the multi-chamber expandable interspinous process brace 1000 includes a central chamber 1002, a superior chamber 1004, and an inferior chamber 1006.

In a particular embodiment, the central chamber 1002 can be generally horizontally elongated. Also, in a particular embodiment, the superior chamber 1004 can be shaped similar to the top half of a letter H and the inferior chamber 1006 can be shaped similar to the bottom half of a letter H. Together, the central chamber 1002, the superior chamber 1004, and the inferior chamber 1006 can be provided in a shape that can generally engage and/or stabilize at least one spinous process, such as, for example, the spinous processes of two adjacent vertebrae. In a particular embodiment, together, the chambers 1002, 1004 and 1006 can be generally H-shaped.

Further, in a particular embodiment, the chambers 1002, 1004, 1006 can be made from one or more expandable biocompatible materials. For example, the materials can be silicones, polyurethanes, polycarbonate urethanes, polyethylene terephthalate, silicone copolymers, polyolefins, or any combination thereof. Also, the chambers 1002, 1004, 1006 can be non-porous or micro-porous, e.g., for venting purposes.

As shown in FIG. 10, the central chamber 1002 can include a first injection tube 1008. The superior chamber 1004 can include a second injection tube 1010 and the inferior chamber 1006 can include a third injection tube 1012. The injection tubes 1008, 1010, 1012 can be used to provide one or more injectable biocompatible material to the chambers 1002, 1004, 1006. In a particular embodiment, each of the central chamber 1002, the superior chamber 1004, and the inferior chamber 1006 of the multi-chamber expandable interspinous process brace 1000 can be expanded from a respective deflated configuration, shown in FIG. 10, to one of a plurality of inflated configurations, shown in FIG. 11 and FIG. 12, up to a maximum inflated configuration. Further, after the chambers 1002, 1004, 1006 are inflated, or otherwise expanded, the injection tubes 1008, 1010, 1012 can be removed, as depicted in FIG. 12.

In a particular embodiment, the multi-chamber expandable interspinous process brace 1000 can include a first self-sealing valve (not shown) within the central chamber 1002, e.g., adjacent to the first injection tube 1008. Moreover, the multi-chamber expandable interspinous process brace 1000 can include a second self-sealing valve (not shown) within the superior chamber 1004, e.g., adjacent to the second injection tube 1010. The multi-chamber expandable interspinous process brace 1000 can also include a third self-sealing valve (not shown) within the inferior chamber 1006. The self-sealing valves can prevent the chambers 1002, 1004, 1006 from leaking material after the chambers 1002, 1004, 1006 are inflated and the injection tubes 1008, 1010, 1012 are removed.

As illustrated in FIG. 10 through FIG. 12, the superior chamber 1004 can include a superior spinous process pocket 1014 and the inferior chamber 1006 can include an inferior spinous process pocket 1016. Further, a superior spinous process engagement structure 1020 can extend from the superior chamber 1004 within the superior spinous process pocket 1014. Also, an inferior spinous process engagement structure 1022 can extend from the inferior chamber 1004 within the inferior spinous process pocket 1016. In a particular embodiment, each of the spinous process engagement structures 1020, 1022 can be one or more spikes, one or more teeth, a combination thereof, or some other structure configured to engage a spinous process.

FIG. 10 through FIG. 12 indicate that the multi-chamber expandable interspinous process brace 1000 can be implanted between a superior spinous process 1100 and an inferior spinous process 1102. In a particular embodiment, the chambers 1002, 1004, 1006 can be inflated so the superior chamber 1004 engages the superior spinous process 1100 and the inferior chamber 1006 engages the inferior spinous process 1102. In a particular embodiment, when the multi-chamber expandable interspinous process brace 1000 is properly installed and inflated between the superior spinous process 1100 and the inferior spinous process 1102, the superior spinous process pocket 1014 can engage and support the superior spinous process 1100. Further, the inferior spinous process pocket 1016 can engage and support an inferior spinous process 1102.

More specifically, the superior spinous process engagement structure 1020 can extend slightly into and engage the superior spinous process 1100. Also, the inferior spinous process engagement structure 1022 can extend slightly into and engage the inferior spinous process 1102. Accordingly, the spinous process engagement structures 1020, 1022, the spinous process pockets 1014, 1016, or a combination thereof can substantially prevent the multi-chamber expandable interspinous process brace 1000 from migrating with respect to the spinous processes 1100, 1102.

Also, in a particular embodiment, the multi-chamber expandable interspinous process brace 1000 can be movable between a deflated configuration, shown in FIG. 10, and one or more inflated configurations, shown in FIG. 11 and FIG. 12. In the deflated configuration, a distance 1112 between the superior spinous process pocket 1014 and the inferior spinous process pocket 1016 can be at a minimum. However, as one or more materials are injected into the chambers 1002, 1004, 1006 the distance 1112 between the superior spinous process pocket 1014 and the inferior spinous process pocket 1016 can increase.

Accordingly, the multi-chamber expandable interspinous process brace 1000 can be installed between a superior spinous process 1100 and an inferior spinous process 1102. Further, the multi-chamber expandable interspinous process brace 1000 can be expanded, e.g., by injecting one or more materials into the chambers 1002, 1004, 1006 in order to increase the distance between the superior spinous process 1100 and the inferior spinous process 1102.

Alternatively, a distractor can be used to increase the distance between the superior spinous process 1100 and the inferior spinous process 1102 and the multi-chamber expandable interspinous process brace 1000 can be expanded to support the superior spinous process 1100 and the inferior spinous process 1102. After the multi-chamber expandable interspinous process brace 1000 is expanded accordingly, the distractor can be removed and the multi-chamber expandable interspinous process brace 1000 can support the superior spinous process 1100 and the inferior spinous process 1102 to substantially prevent the distance between the superior spinous process 1102 and the inferior spinous process 1100 from returning to a pre-distraction value.

In a particular embodiment, the multi-chamber expandable interspinous process brace 1000 can be injected with one or more injectable biocompatible materials that remain elastic after curing. Further, the injectable biocompatible materials can include polymer materials that remain elastic after curing. Also, the injectable biocompatible materials can include ceramics.

For example, the polymer materials can include polyurethanes, polyolefins, silicones, silicone polyurethane copolymers, polymethylmethacrylate (PMMA), epoxies, cyanoacrylates, hydrogels, or a combination thereof. Further, the polyolefin materials can include polypropylenes, polyethylenes, halogenated polyolefins, or flouropolyolefins.

The hydrogels can include polyacrylamide (PAAM), poly-N-isopropylacrylamine (PNIPAM), polyvinyl methylether (PVM), polyvinyl alcohol (PVA), polyethyl hydroxyethyl cellulose, poly (2-ethyl) oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or a combination thereof.

In a particular embodiment, the ceramics can include calcium phosphate, hydroxyapatite, calcium sulfate, bioactive glass, or a combination thereof. In an alternative embodiment, the injectable biocompatible materials can include one or more fluids such as sterile water, saline, or sterile air.

In a particular embodiment, the hardness of the material used to inflate the central chamber 1002 can be less than or equal to the hardness of the material used to inflate the superior chamber 1004 and the inferior chamber 1006, i.e., after the materials used to inflate the central chamber 1002, the superior chamber 1004, and the inferior chamber 1006 are cured. Alternatively, the viscosity of the material used to inflate the central chamber 1002 can be less than or equal to the viscosity of the material used to inflate the superior chamber 1004 and the inferior chamber 1006. In a particular embodiment, certain or all of the injected materials can be cured or cross-linked in situ to form a solid interspinous process brace with non-uniform bulk properties.

FIG. 12 indicates that a tether 1200 can be installed around the multi-chamber expandable interspinous process brace 1000, after the multi-chamber expandable interspinous process brace 1000 is expanded as described herein. As shown, the tether 1200 can include a proximal end 1202 and a distal end 1204. In a particular embodiment, the tether 1200 can circumscribe the multi-chamber expandable interspinous process brace 1000 and the spinous processes 1100, 1102. Further, the ends 1202, 1204 of the tether 1200 can be brought together and one or more fasteners can be installed therethrough to connect the ends 1202, 1204. Accordingly, the tether 1200 can be installed in order to prevent the distance between the spinous processes 1100, 1102 from substantially increasing beyond the distance provided by the multi-chamber expandable interspinous process brace 1000 after it is expanded and to maintain engagement of the interspinous processes with the spinous process pockets 1014, 1016, engagement structures 1020, 1022, or a combination thereof.

In a particular embodiment, the tether 1200 can comprise a biocompatible elastomeric material that flexes during installation and provides a resistance fit against the inferior process. Further, the tether 1200 can comprise a substantially non-resorbable suture or the like.

Figure 13:
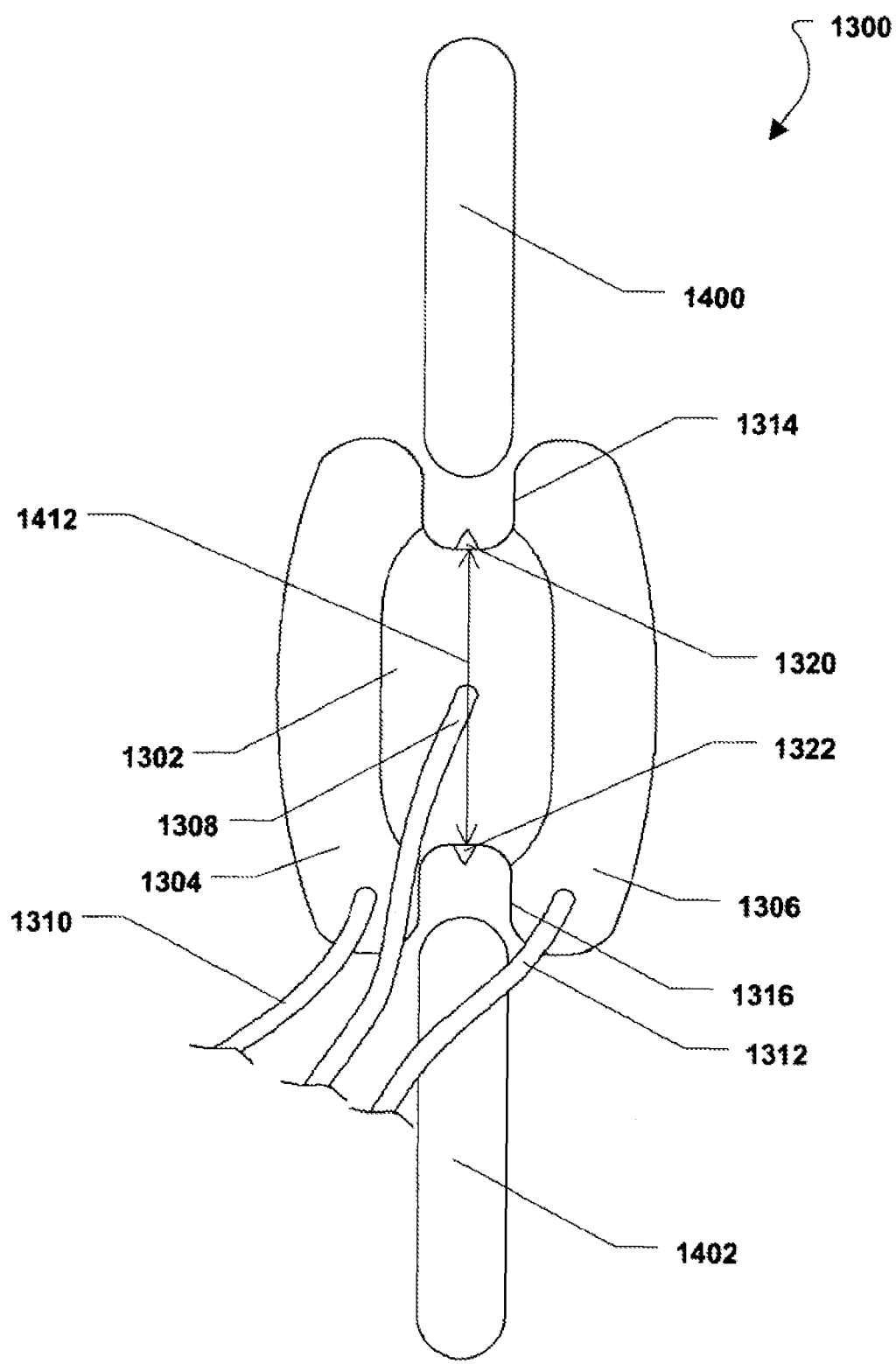
FIG. 13 is a plan view of a fourth multi-chamber expandable interspinous process spacer in a deflated configuration.
Figure 14:
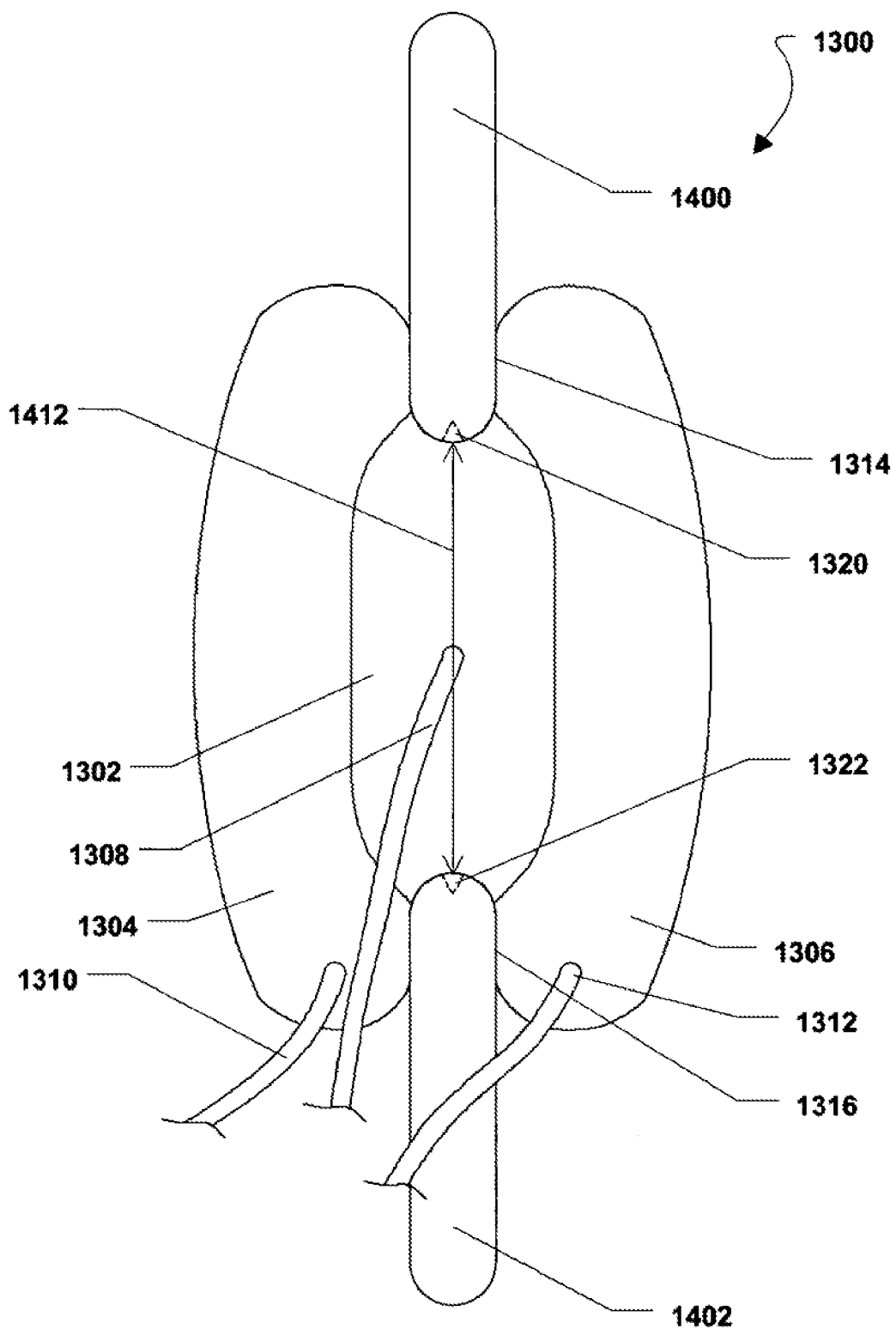
FIG. 14 is a plan view of the fourth multi-chamber expandable interspinous process spacer in an inflated configuration.
Figure 15:
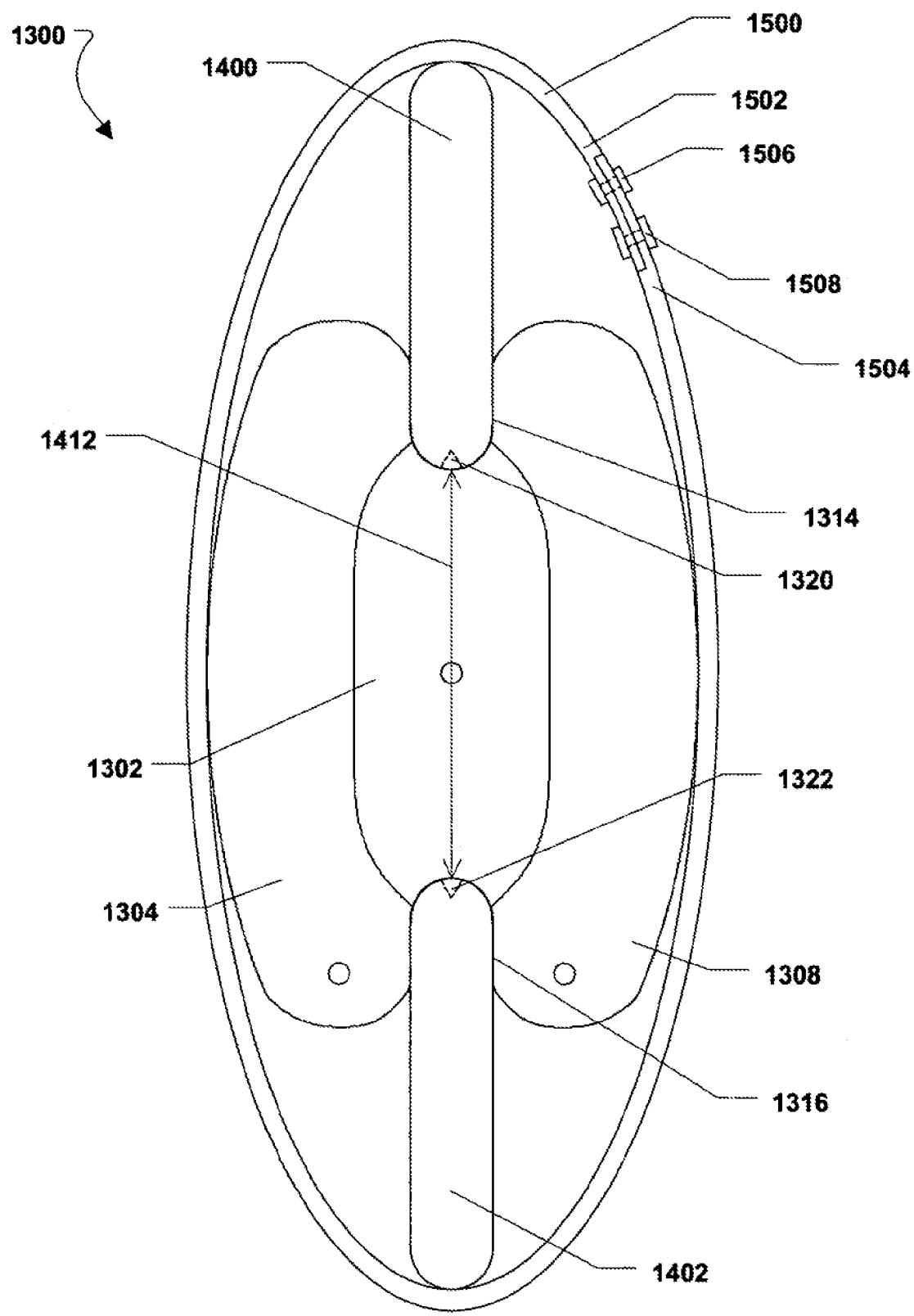
FIG. 15 is a plan view of the fourth multi-chamber expandable interspinous process spacer in an inflated configuration with a tether installed there around.

Description of a Fourth Embodiment of a Multi-Chamber Expandable Interspinous Process Brace Referring to FIG. 13 through FIG. 15, a fourth embodiment of a multi-chamber expandable interspinous process brace is shown and is generally designated 1300. As shown, the multi-chamber expandable interspinous process brace 1300 includes a central chamber 1302, a first lateral chamber 1304, and a second lateral chamber 1306.

In a particular embodiment, the central chamber 1302 can be generally vertically elongated. Also, in a particular embodiment, the first lateral chamber 1304 can be vertically elongated and can extend along a first side of the central chamber 1302. The second lateral chamber 1306 can also be vertically elongated and can extend along a second side of the central chamber 1302. As shown, the lateral chambers 1304, 1306 can extend beyond a top and bottom of the central chamber 1302. Together, the central chamber 1302, the first lateral chamber 1304, and the second lateral chamber 1306 can be provided in a shape that can generally engage and/or stabilize at least one spinous process, such as, for example, the spinous processes of two adjacent vertebrae. In a particular embodiment, together, the chambers 1302, 1304 and 1306 can be generally H-shaped.

Further, in a particular embodiment, the chambers 1302, 1304, 1306 can be made from one or more expandable biocompatible materials. For example, the materials can be silicones, polyurethanes, polycarbonate urethanes, polyethylene terephthalate, silicone copolymers, polyolefins, or any combination thereof. Also, the chambers 1302, 1304, 1306 can be non-porous or micro-porous, e.g., for venting purposes.

As shown in FIG. 13, the central chamber 1302 can include a first injection tube 1308. The first lateral chamber 1304 can include a second injection tube 1310 and the second lateral chamber 1306 can include a third injection tube 1312. The injection tubes 1308, 1310, 1312 can be used to provide one or more injectable biocompatible material to the chambers 1302, 1304, 1306. In a particular embodiment, each of the central chamber 1302, the first lateral chamber 1304, and the second lateral chamber 1306 of the multi-chamber expandable interspinous process brace 1300 can be expanded from a respective deflated configuration, shown in FIG. 13, to one of a plurality of inflated configurations, shown in FIG. 14 and FIG. 15, up to a maximum inflated configuration. Further, after the chambers 1302, 1304, 1306 are inflated, or otherwise expanded, the injection tubes 1308, 1310, 1312 can be removed, as depicted in FIG. 15.

In a particular embodiment, the multi-chamber expandable interspinous process brace 1300 can include a first self-sealing valve (not shown) within the central chamber 1302, e.g., adjacent to the first injection tube 1308. Moreover, the multi-chamber expandable interspinous process brace 1300 can include a second self-sealing valve (not shown) within the first lateral chamber 1304, e.g., adjacent to the second injection tube 1310. The multi-chamber expandable interspinous process brace 1300 can also include a third self-sealing valve (not shown) within the second lateral chamber 1306. The self-sealing valves can prevent the chambers 1302, 1304, 1306 from leaking material after the chambers 1302, 1304, 1306 are inflated and the injection tubes 1308, 1310, 1312 are removed.

As illustrated in FIG. 13 through FIG. 15, the multi-chamber expandable interspinous process brace 1300 can include a superior spinous process pocket 1314 that is formed by a top portion of the central chamber 1302, a top portion of the first lateral chamber 1304, and a top portion of the second lateral chamber 1306. The multi-chamber expandable interspinous process brace 1300 can also include an inferior spinous process pocket 1316 that can be formed by a bottom portion of the central chamber 1302, a bottom portion of the first lateral chamber 1304, and a bottom portion of the second lateral chamber 1306.

Further, a superior spinous process engagement structure 1320 can extend from the central chamber 1304 within the superior spinous process pocket 1314. Also, an inferior spinous process engagement structure 1322 can extend from the central chamber 1304 within the inferior spinous process pocket 1316. In a particular embodiment, each of the spinous process engagement structures 1320, 1322 can be one or more spikes, one or more teeth, a combination thereof, or some other structure configured to engage a spinous process.

FIG. 13 through FIG. 15 indicate that the multi-chamber expandable interspinous process brace 1300 can be implanted between a superior spinous process 1400 and an inferior spinous process 1402. In a particular embodiment, the chambers 1302, 1304, 1306 can be inflated so the superior spinous process pocket 1314 can engage and support the superior spinous process 1400 and so the inferior spinous process pocket 1316 can engage and support an inferior spinous process 1402.

More specifically, the superior spinous process engagement structure 1320 can extend slightly into and engage the superior spinous process 1400. Also, the inferior spinous process engagement structure 1322 can extend slightly into and engage the inferior spinous process 1402. Accordingly, the spinous process engagement structures 1320, 1322, the spinous process pockets 1314, 1316, or a combination thereof can substantially prevent the multi-chamber expandable interspinous process brace 1300 from migrating with respect to the spinous processes 1400, 1402.

Also, in a particular embodiment, the multi-chamber expandable interspinous process brace 1300 can be movable between a deflated configuration, shown in FIG. 13, and one or more inflated configurations, shown in FIG. 14 and FIG. 15. In the deflated configuration, a distance 1412 between the superior spinous process pocket 1314 and the inferior spinous process pocket 1316 can be at a minimum. However, as one or more materials are injected into the chambers 1302, 1304, 1306 the distance 1412 between the superior spinous process pocket 1314 and the inferior spinous process pocket 1316 can increase.

Accordingly, the multi-chamber expandable interspinous process brace 1300 can be installed between a superior spinous process 1400 and an inferior spinous process 1402. Further, the multi-chamber expandable interspinous process brace 1300 can be expanded, e.g., by injecting one or more materials into the chambers 1302, 1304, 1306 in order to increase the distance between the superior spinous process 1400 and the inferior spinous process 1402.

Alternatively, a distractor can be used to increase the distance between the superior spinous process 1400 and the inferior spinous process 1402 and the multi-chamber expandable interspinous process brace 1300 can be expanded to support the superior spinous process 1400 and the inferior spinous process 1402. After the multi-chamber expandable interspinous process brace 1300 is expanded accordingly, the distractor can be removed and the multi-chamber expandable interspinous process brace 1300 can support the superior spinous process 1400 and the inferior spinous process 1402 to substantially prevent the distance between the superior spinous process 1402 and the inferior spinous process 1400 from returning to a pre-distraction value.

In a particular embodiment, the multi-chamber expandable interspinous process brace 1300 can be injected with one or more injectable biocompatible materials that remain elastic after curing. Further, the injectable biocompatible materials can include polymer materials that remain elastic after curing. Also, the injectable biocompatible materials can include ceramics.

For example, the polymer materials can include polyurethanes, polyolefins, silicones, silicone polyurethane copolymers, polymethylmethacrylate (PMMA), epoxies, cyanoacrylates, hydrogels, or a combination thereof. Further, the polyolefin materials can include polypropylenes, polyethylenes, halogenated polyolefins, or flouropolyolefins.

The hydrogels can include polyacrylamide (PAAM), poly-N-isopropylacrylamine (PNIPAM), polyvinyl methylether (PVM), polyvinyl alcohol (PVA), polyethyl hydroxyethyl cellulose, poly (2-ethyl) oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or a combination thereof.

In a particular embodiment, the ceramics can include calcium phosphate, hydroxyapatite, calcium sulfate, bioactive glass, or a combination thereof. In an alternative embodiment, the injectable biocompatible materials can include one or more fluids such as sterile water, saline, or sterile air.

In a particular embodiment, the hardness of the material used to inflate the central chamber 1302 can be less than or equal to the hardness of the material used to inflate the first lateral chamber 1304 and the second lateral chamber 1306, i.e., after the materials used to inflate the central chamber 1302, the first lateral chamber 1304, and the second lateral chamber 1306 are cured. Alternatively, the viscosity of the material used to inflate the central chamber 1302 can be less than or equal to the viscosity of the material used to inflate the first lateral chamber 1304 and the second lateral chamber 1306. In a particular embodiment, certain or all of the injected materials can be cured or cross-linked in situ to form a solid interspinous process brace with non-uniform bulk properties.

FIG. 15 indicates that a tether 1500 can be installed around the multi-chamber expandable interspinous process brace 1300, after the multi-chamber expandable interspinous process brace 1300 is expanded as described herein. As shown, the tether 1500 can include a proximal end 1502 and a distal end 1504. In a particular embodiment, the tether 1500 can circumscribe the multi-chamber expandable interspinous process brace 1300 and the spinous processes 1400, 1402. Further, the ends 1502, 1504 of the tether 1500 can be brought together and one or more fasteners can be installed therethrough to connect the ends 1502, 1504. Accordingly, the tether 1500 can be installed in order to prevent the distance between the spinous processes 1400, 1402 from substantially increasing beyond the distance provided by the multi-chamber expandable interspinous process brace 1300 after it is expanded and to maintain engagement of the interspinous processes with the spinous process pockets 1314, 1316, engagement structures 1320, 1322, or a combination thereof.

In a particular embodiment, the tether 1500 can comprise a biocompatible elastomeric material that flexes during installation and provides a resistance fit against the inferior process. Further, the tether 1500 can comprise a substantially non-resorbable suture or the like.

Figure 16:
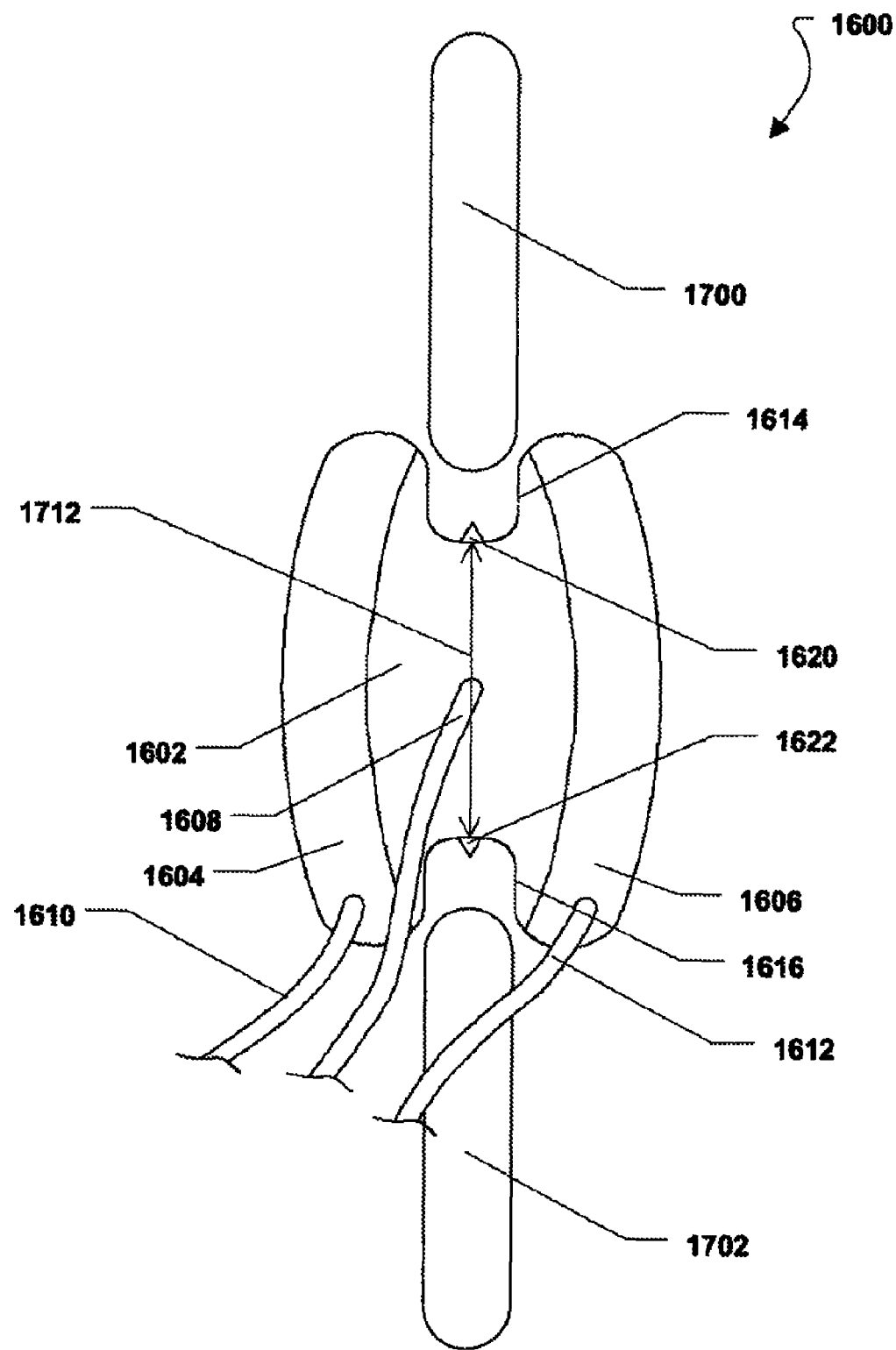
FIG. 16 is a plan view of a fifth multi-chamber expandable interspinous process spacer in a deflated configuration.
Figure 17:
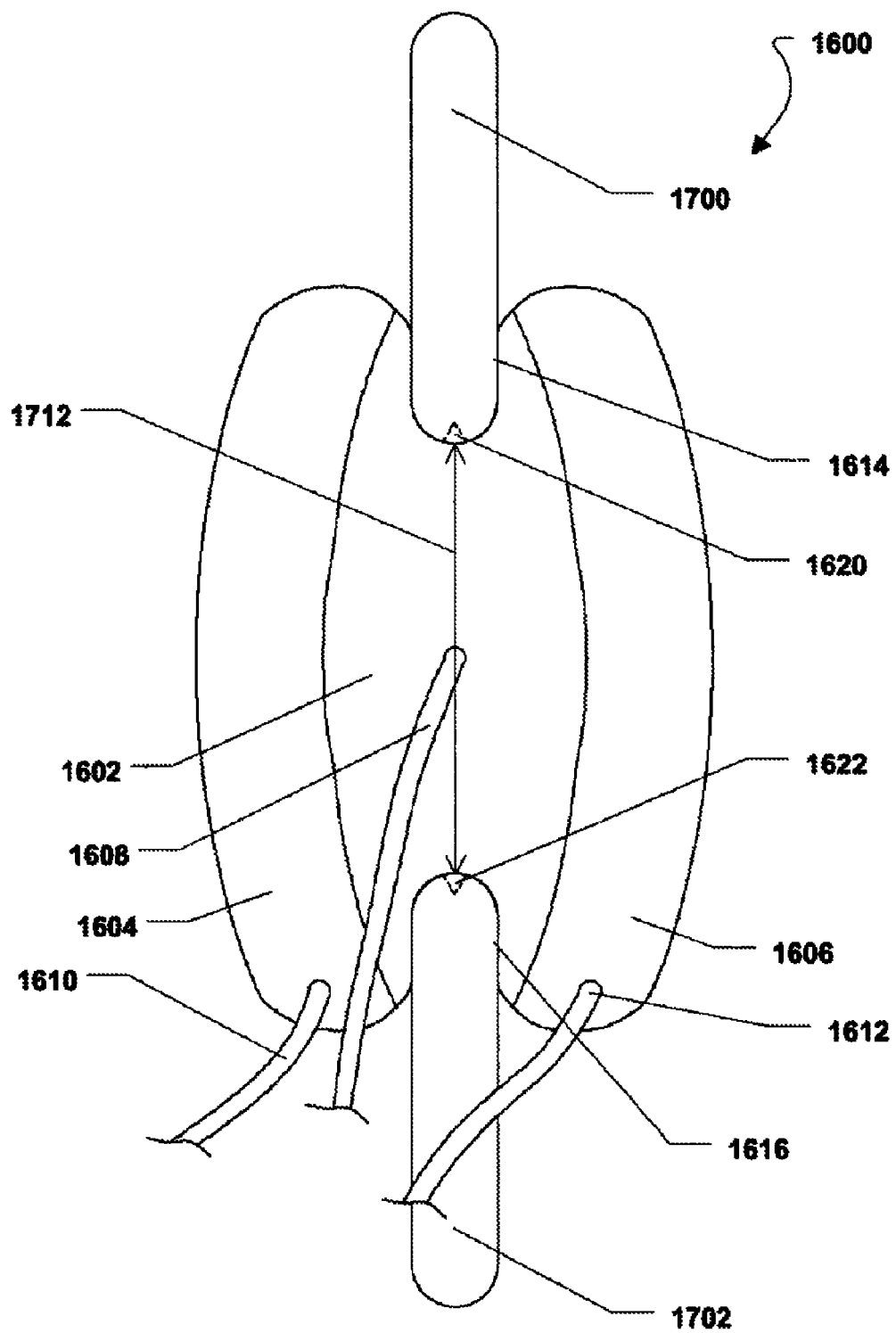
FIG. 17 is a plan view of the fifth multi-chamber expandable interspinous process spacer in an inflated configuration.
Figure 18:
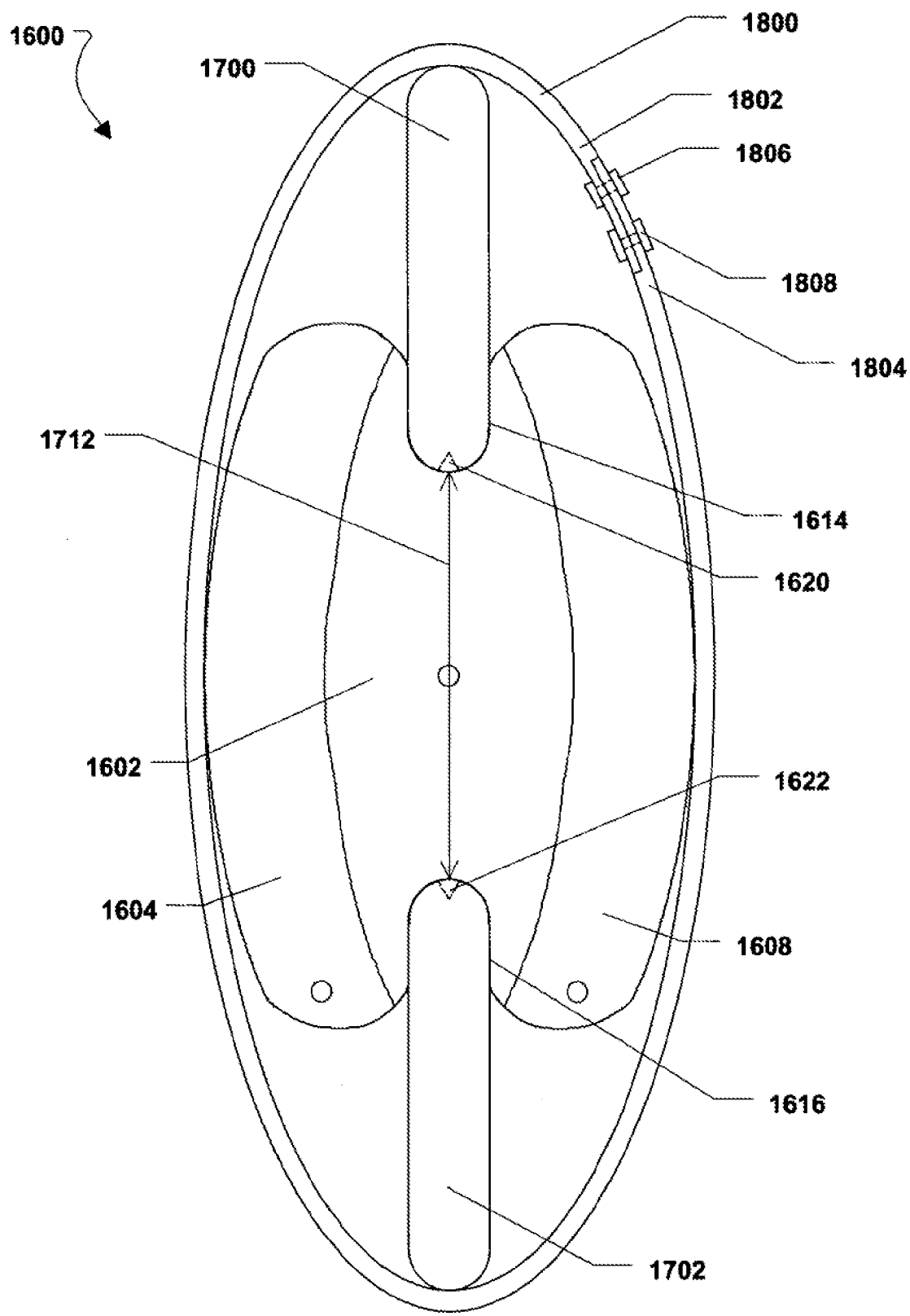
FIG. 18 is a plan view of the fifth multi-chamber expandable interspinous process spacer in an inflated configuration with a tether installed there around.

Description of a Fifth Embodiment of a
Multi-Chamber Expandable Interspinous Process Brace Referring to FIG. 16 through FIG. 18, a fifth embodiment of a multi-chamber expandable interspinous process brace is shown and is generally designated 1600. As shown, the multi-chamber expandable interspinous process brace 1600 includes a central chamber 1602, a first lateral chamber 1604, and a second lateral chamber 1606.

In a particular embodiment, the central chamber 1602 can be generally vertically elongated. Also, in a particular embodiment, the first lateral chamber 1604 can be vertically elongated and can extend along a first side of the central chamber 1602. The second lateral chamber 1606 can also be vertically elongated and can extend along a second side of the central chamber 1602. Together, the central chamber 1602, the first lateral chamber 1604, and the second lateral chamber 1606 can be provided in a shape that can generally engage and/or stabilize at least one spinous process, such as, for example, the spinous processes of two adjacent vertebrae. In a particular embodiment, together, the chambers 1602, 1604 and 1606 can be generally H-shaped.

Further, in a particular embodiment, the chambers 1602, 1604, 1606 can be made from one or more expandable biocompatible materials. For example, the materials can be silicones, polyurethanes, polycarbonate urethanes, polyethylene terephthalate, silicone copolymers, polyolefins, or any combination thereof. Also, the chambers 1602, 1604, 1606 can be non-porous or micro-porous, e.g., for venting purposes.

As shown in FIG. 16, the central chamber 1602 can include a first injection tube 1608. The first lateral chamber 1604 can include a second injection tube 1610 and the second lateral chamber 1606 can include a third injection tube 1612. The injection tubes 1608, 1610, 1612 can be used to provide one or more injectable biocompatible material to the chambers 1602, 1604, 1606. In a particular embodiment, each of the central chamber 1602, the first lateral chamber 1604, and the second lateral chamber 1606 of the multi-chamber expandable interspinous process brace 1600 can be expanded from a respective deflated configuration, shown in FIG. 16, to one of a plurality of inflated configurations, shown in FIG. 17 and FIG. 18, up to a maximum inflated configuration. Further, after the chambers 1602, 1604, 1606 are inflated, or otherwise expanded, the injection tubes 1608, 1610, 1612 can be removed, as depicted in FIG. 18.

In a particular embodiment, the multi-chamber expandable interspinous process brace 1600 can include a first self-sealing valve (not shown) within the central chamber 1602, e.g., adjacent to the first injection tube 1608. Moreover, the multi-chamber expandable interspinous process brace 1600 can include a second self-sealing valve (not shown) within the first lateral chamber 1604, e.g., adjacent to the second injection tube 1610. The multi-chamber expandable interspinous process brace 1600 can also include a third self-sealing valve (not shown) within the second lateral chamber 1606. The self-sealing valves can prevent the chambers 1602, 1604, 1606 from leaking material after the chambers 1602, 1604, 1606 are inflated and the injection tubes 1608, 1610, 1612 are removed.

As illustrated in FIG. 16 through FIG. 18, central chamber 1602 of the multi-chamber expandable interspinous process brace 1600 can include a superior spinous process pocket 1614. The central chamber 1602 of the multi-chamber expandable interspinous process brace 1600 can also include an inferior spinous process pocket 1616. Further, a superior spinous process engagement structure 1620 can extend from the central chamber 1604 within the superior spinous process pocket 1614. Also, an inferior spinous process engagement structure 1622 can extend from the central chamber 1604 within the inferior spinous process pocket 1616. In a particular embodiment, each of the spinous process engagement structures 1620, 1622 can be one or more spikes, one or more teeth, a combination thereof, or some other structure configured to engage a spinous process.

FIG. 16 through FIG. 18 indicate that the multi-chamber expandable interspinous process brace 1600 can be implanted between a superior spinous process 1700 and an inferior spinous process 1702. In a particular embodiment, the chambers 1602, 1604, 1606 can be inflated so the superior spinous process pocket 1614 can engage and support the superior spinous process 1700 and so the inferior spinous process pocket 1616 can engage and support an inferior spinous process 1702.

More specifically, the superior spinous process engagement structure 1620 can extend slightly into and engage the superior spinous process 1700. Also, the inferior spinous process engagement structure 1622 can extend slightly into and engage the inferior spinous process 1702. Accordingly, the spinous process engagement structures 1620, 1622, the spinous process pockets 1614, 1616, or a combination thereof can substantially prevent the multi-chamber expandable interspinous process brace 1600 from migrating with respect to the spinous processes 1700, 1702.

Also, in a particular embodiment, the multi-chamber expandable interspinous process brace 1600 can be movable between a deflated configuration, shown in FIG. 16, and one or more inflated configurations, shown in FIG. 17 and FIG. 18. In the deflated configuration, a distance 1712 between the superior spinous process pocket 1614 and the inferior spinous process pocket 1616 can be at a minimum. However, as one or more materials are injected into the chambers 1602, 1604, 1606 the distance 1712 between the superior spinous process pocket 1614 and the inferior spinous process pocket 1616 can increase.

Accordingly, the multi-chamber expandable interspinous process brace 1600 can be installed between a superior spinous process 1700 and an inferior spinous process 1702. Further, the multi-chamber expandable interspinous process brace 1600 can be expanded, e.g., by injecting one or more materials into the chambers 1602, 1604, 1606 in order to increase the distance between the superior spinous process 1700 and the inferior spinous process 1702.

Alternatively, a distractor can be used to increase the distance between the superior spinous process 1700 and the inferior spinous process 1702 and the multi-chamber expandable interspinous process brace 1600 can be expanded to support the superior spinous process 1700 and the inferior spinous process 1702. After the multi-chamber expandable interspinous process brace 1600 is expanded accordingly, the distractor can be removed and the multi-chamber expandable interspinous process brace 1600 can support the superior spinous process 1700 and the inferior spinous process 1702 to substantially prevent the distance between the superior spinous process 1702 and the inferior spinous process 1700 from returning to a pre-distraction value.

In a particular embodiment, the multi-chamber expandable interspinous process brace 1600 can be injected with one or more injectable biocompatible materials that remain elastic after curing. Further, the injectable biocompatible materials can include polymer materials that remain elastic after curing. Also, the injectable biocompatible materials can include ceramics.

For example, the polymer materials can include polyurethanes, polyolefins, silicones, silicone polyurethane copolymers, polymethylmethacrylate (PMMA), epoxies, cyanoacrylates, hydrogels, or a combination thereof. Further, the polyolefin materials can include polypropylenes, polyethylenes, halogenated polyolefins, or flouropolyolefins.

The hydrogels can include polyacrylamide (PAAM), poly-N-isopropylacrylamine (PNIPAM), polyvinyl methylether (PVM), polyvinyl alcohol (PVA), polyethyl hydroxyethyl cellulose, poly (2-ethyl) oxazoline, polyethyleneoxide (PEO), polyethylglycol' (PEG), polyacrylacid (PAA), polyacrylonitrile (PAN), polyvinylacrylate (PVA), polyvinylpyrrolidone (PVP), or a combination thereof.

In a particular embodiment, the ceramics can include calcium phosphate, hydroxyapatite, calcium sulfate, bioactive glass, or a combination thereof. In an alternative embodiment, the injectable biocompatible materials can include one or more fluids such as sterile water, saline, or sterile air.

In a particular embodiment, the hardness of the material used to inflate the central chamber 1602 can be less than or equal to the hardness of the material used to inflate the first lateral chamber 1604 and the second lateral chamber 1606, i.e., after the materials used to inflate the central chamber 1602, the first lateral chamber 1604, and the second lateral chamber 1606 are cured. Alternatively, the viscosity of the material used to inflate the central chamber 1602 can be less than or equal to the viscosity of the material used to inflate the first lateral chamber 1604 and the second lateral chamber 1606. In a particular embodiment, certain or all of the injected materials can be cured or cross-linked in situ to form a solid interspinous process brace with non-uniform bulk properties.

FIG. 18 indicates that a tether 1800 can be installed around the multi-chamber expandable interspinous process brace 1600, after the multi-chamber expandable interspinous process brace 1600 is expanded as described herein. As shown, the tether 1800 can include a proximal end 1802 and a distal end 1804. In a particular embodiment, the tether 1800 can circumscribe the multi-chamber expandable interspinous process brace 1600 and the spinous processes 1700, 1702. Further, the ends 1802, 1804 of the tether 1800 can be brought together and one or more fasteners can be installed therethrough to connect the ends 1802, 1804. Accordingly, the tether 1800 can be installed in order to prevent the distance between the spinous processes 1700, 1702 from substantially increasing beyond the distance provided by the multi-chamber expandable interspinous process brace 1600 after it is expanded and to maintain engagement of the interspinous processes with the spinous process pockets 1614, 1616, engagement structures 1620, 1622, or a combination thereof.

In a particular embodiment, the tether 1800 can comprise a biocompatible elastomeric material that flexes during installation and provides a resistance fit against the inferior process. Further, the tether 1800 can comprise a substantially non-resorbable suture or the like.

Figure 19:
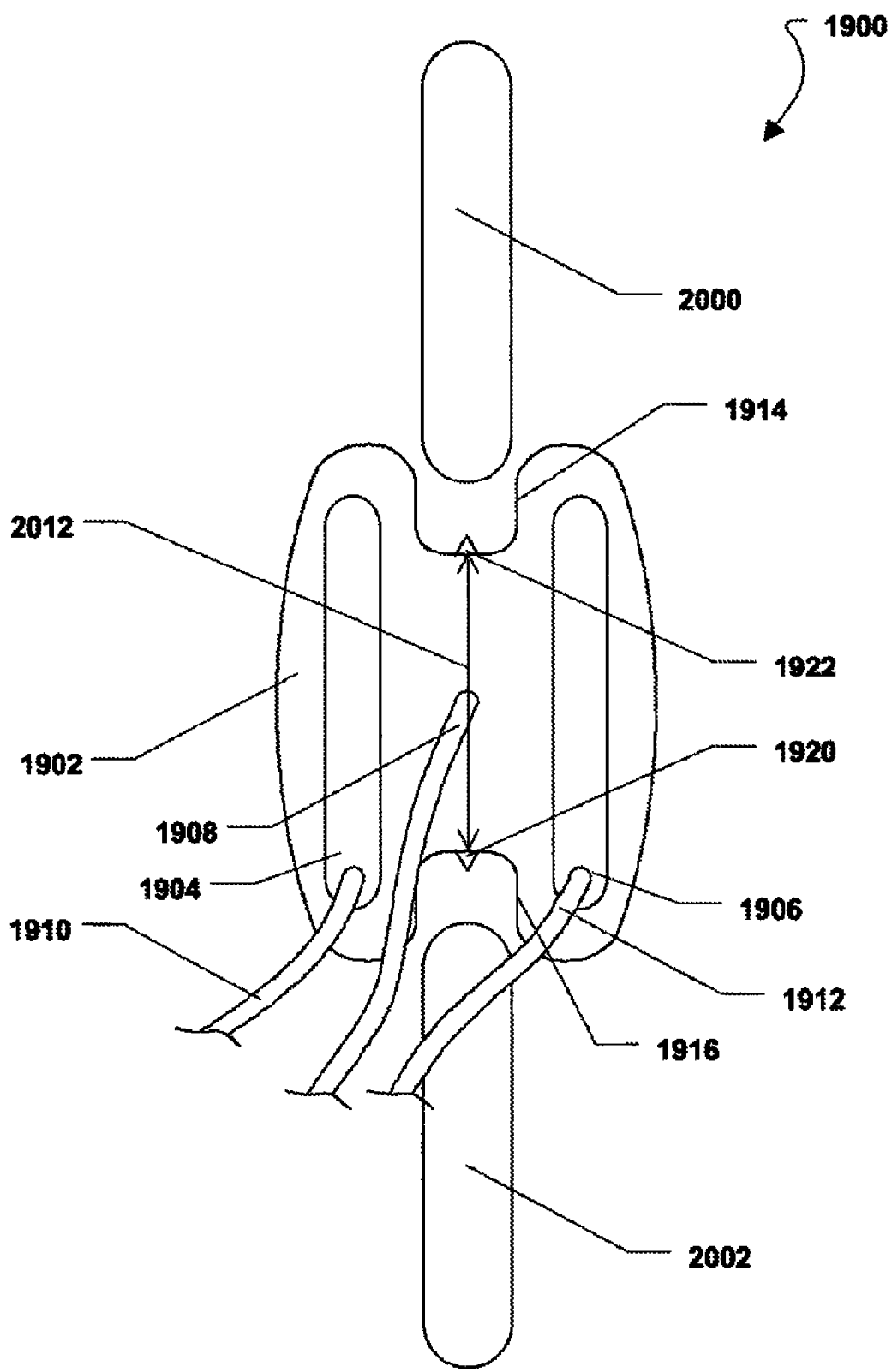
FIG. 19 is a plan view of a sixth multi-chamber expandable interspinous process spacer in a deflated configuration.
Figure 20:
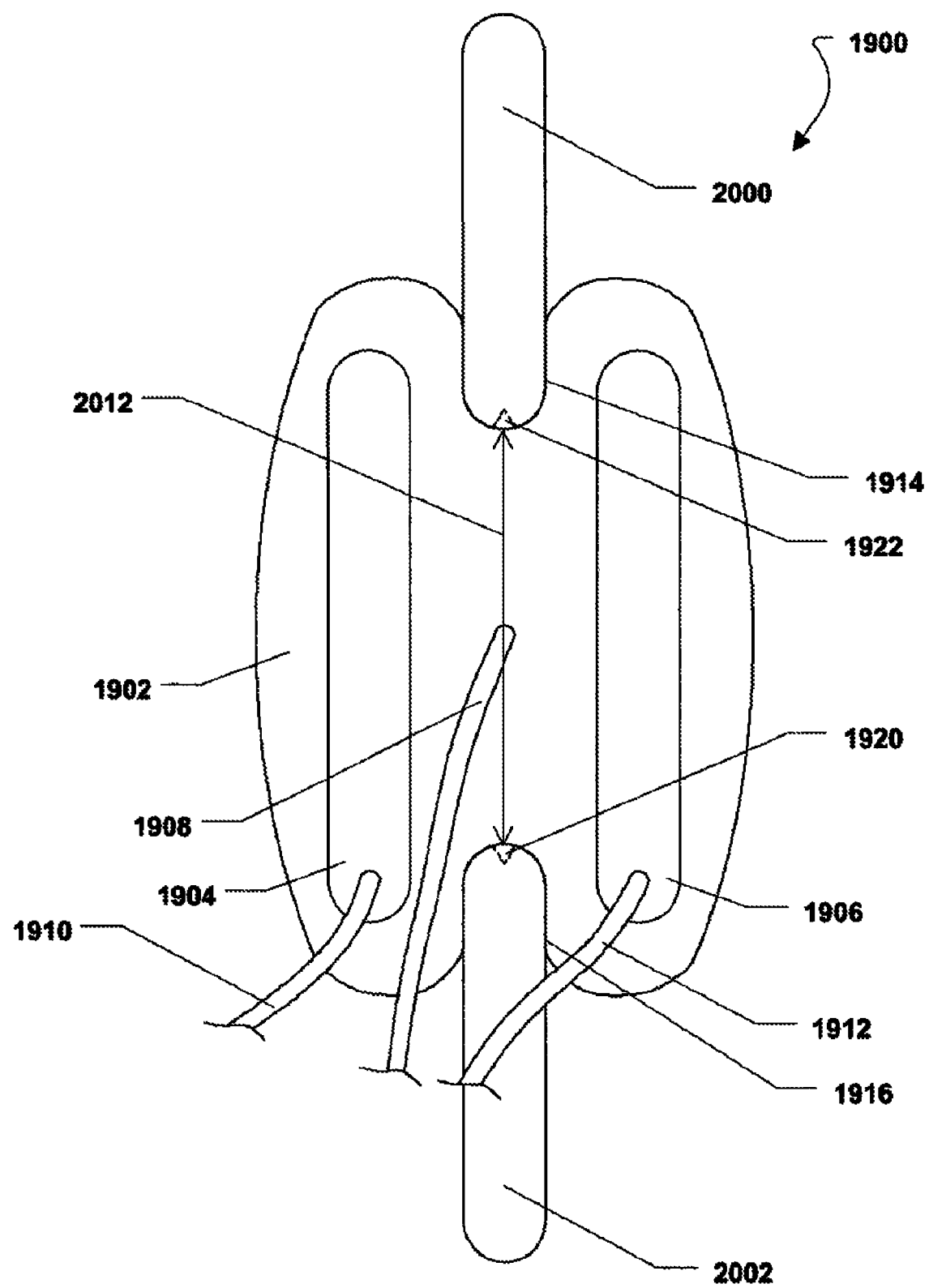
FIG. 20 is a plan view of the sixth multi-chamber expandable interspinous process spacer in an inflated configuration.
Figure 21:
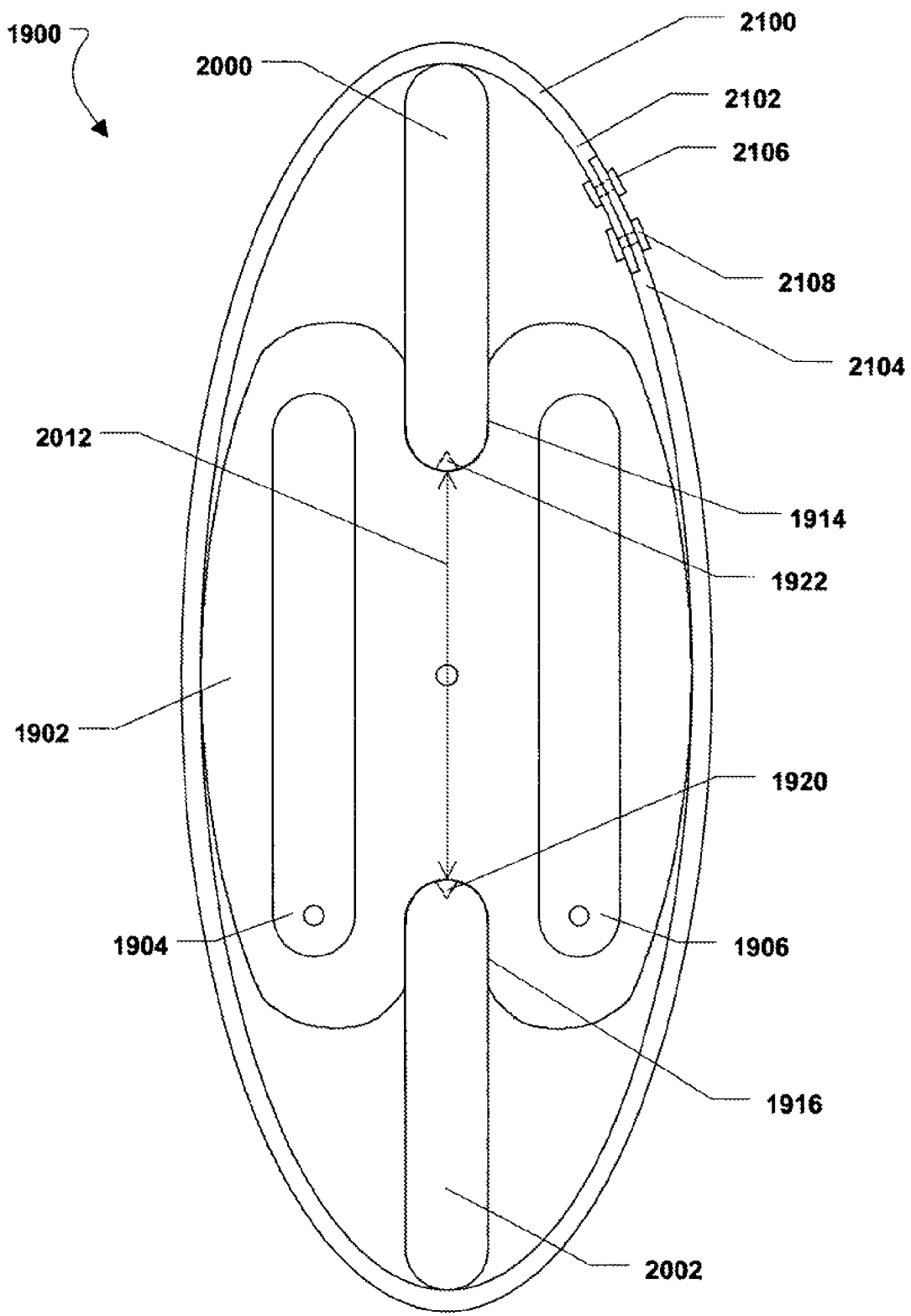
FIG. 21 is a plan view of the sixth multi-chamber expandable interspinous process spacer in an inflated configuration with a tether installed there around.

Description of a Sixth Embodiment of a Multi-Chamber Expandable Interspinous Process Brace Referring to FIG. 19 through FIG. 21, a sixth embodiment of a multi-chamber expandable interspinous process brace is shown and is generally designated 1900. As shown, the multi-chamber expandable interspinous process brace 1900 includes an exterior chamber 1902, a first interior chamber 1904, and a second interior chamber 1906.

In a particular embodiment, the exterior chamber 1902 can be provided in a shape that can generally engage and/or stabilize at least one spinous process, such as, for example, the spinous processes of two adjacent vertebrae. In a particular embodiment, the exterior chamber 1902 can be generally H-shaped. Also, in a particular embodiment, the first interior chamber 1904 can be vertically elongated and can be disposed within a first side of the exterior chamber 1902. The second interior chamber 1906 can also be vertically elongated and can be disposed within a second side of the exterior chamber 1902.

Further, in a particular embodiment, the chambers 1902, 1904, 1906 can be made from one or more expandable biocompatible materials. For example, the materials can be silicones, polyurethanes, polycarbonate urethanes, polyethylene terephthalate, silicone copolymers, polyolefins, or any combination thereof. Also, the chambers 1902, 1904, 1906 can be non-porous or micro-porous, e.g., for venting purposes.

As shown in FIG. 19, the exterior chamber 1902 can include a first injection tube 1908. The first interior chamber 1904 can include a second injection tube 1910 and the second interior chamber 1906 can include a third injection tube 1912. The injection tubes 1908, 1910, 1912 can be used to provide one or more injectable biocompatible material to the chambers 1902, 1904, 1906. In a particular embodiment, each of the exterior chamber 1902, the first interior chamber 1904, and the second interior chamber 1906 of the multi-chamber expandable interspinous process brace 1900 can be expanded from a respective deflated configuration, shown in FIG. 19, to one of a plurality of inflated configurations, shown in FIG. 20 and FIG. 21, up to a maximum inflated configuration. Further, after the chambers 1902, 1904, 1906 are inflated, or otherwise expanded, the injection tubes 1908, 1910, 1912 can be removed, as depicted in FIG. 21.

In a particular embodiment, the multi-chamber expandable interspinous process brace 1900 can include a first self-sealing valve (not shown) within the exterior chamber 1902, e.g., adjacent to the first injection tube 1908. Moreover, the multi-chamber expandable interspinous process brace 1900 can include a second self-sealing valve (not shown) within the first interior chamber 1904, e.g., adjacent to the second injection tube 1910. The multi-chamber expandable interspinous process brace 1900 can also include a third self-sealing valve (not shown) within the second interior chamber 1906. The self-sealing valves can prevent the chambers 1902, 1904, 1906 from leaking material after the chambers 1902, 1904, 1906 are inflated and the injection tubes 1908, 1910, 1912 are removed.

As illustrated in FIG. 19 through FIG. 21, exterior chamber 1902 of the multi-chamber expandable interspinous process brace 1900 can include a superior spinous process pocket 1914. The exterior chamber 1902 of the multi-chamber expandable interspinous process brace 1900 can also include an inferior spinous process pocket 1916. Further, a superior spinous process engagement structure 1922 can extend from the exterior chamber 1902 within the superior spinous process pocket 1914. Also, an inferior spinous process engagement structure 1920 can extend from the exterior chamber 1902 within the inferior spinous process pocket 1916. In a particular embodiment, each of the spinous process engagement structures 1920, 1922 can be one or more spikes, one or more teeth, a combination thereof, or some other structure configured to engage a spinous process.

FIG. 19 through FIG. 21 indicate that the multi-chamber expandable interspinous process brace 1900 can be implanted between a superior spinous process 2000 and an inferior spinous process 2002. In a particular embodiment, the chambers 1902, 1904, 1906 can be inflated so the superior spinous process pocket 1914 can engage and support the superior spinous process 2000 and so the inferior spinous process pocket 1916 can engage and support an inferior spinous process 2002.

More specifically, the superior spinous process engagement structure 1922 can extend slightly into and engage the superior spinous process 2000. Also, the inferior spinous process engagement structure 1920 can extend slightly into and engage the inferior spinous process 2002. Accordingly, the spinous process engagement structures 1920, 1922, the spinous process pockets 1914, 1916, or a combination thereof can substantially prevent the multi-chamber expandable interspinous process brace 1900 from migrating with respect to the spinous processes 2000, 2002.

Also, in a particular embodiment, the multi-chamber expandable interspinous process brace 1900 can be movable between a deflated configuration, shown in FIG. 19, and one or more inflated configurations, shown in FIG. 20 and FIG. 21. In the deflated configuration, a distance 2012 between the superior spinous process pocket 1914 and the inferior spinous process pocket 1916 can be at a minimum. However, as one or more materials are injected into the chambers 1902, 1904, 1906 the distance 2012 between the superior spinous process pocket 1914 and the inferior spinous process pocket 1916 can increase.

Accordingly, the multi-chamber expandable interspinous process brace 1900 can be installed between a superior spinous process 2000 and an inferior spinous process 2002. Further, the multi-chamber expandable interspinous process brace 1900 can be expanded, e.g., by injecting one or more materials into the chambers 1902, 1904, 1906 in order to increase the distance between the superior spinous process 2000 and the inferior spinous process 2002.

Alternatively, a distractor can be used to increase the distance between the superior spinous process 2000 and the inferior spinous process 2002 and the multi-chamber expandable interspinous process brace 1900 can be expanded to support the superior spinous process 2000 and the inferior spinous process 2002. After the multi-chamber expandable interspinous process brace 1900 is expanded accordingly, the distractor can be removed and the multi-chamber expandable interspinous process brace 1900 can support the superior spinous process 2000 and the inferior spinous process 2002 to substantially prevent the distance between the superior spinous process 2002 and the inferior spinous process 2000 from returning to a pre-distraction value.

In a particular embodiment, the multi-chamber expandable interspinous process brace 1900 can be injected with one or more injectable biocompatible materials that remain elastic after curing. Further, the injectable biocompatible materials can include polymer materials that remain elastic after curing. Also, the injectable biocompatible materials can include ceramics.

For example, the polymer materials can include polyurethanes, polyolefins, silicones, silicone polyurethane copolymers, polymethylmethacrylate (PMMA), epoxies, cyanoacrylates, hydrogels, or a combination thereof. Further, the polyolefin materials can include polypropylenes, polyethylenes, halogenated polyolefins, or flouropolyolefins.

The hydrogels can include polyacrylamide (PAAM), poly-N-isopropylacrylamine (PNIPAM), polyvinyl methylether (PVM), polyvinyl alcohol (PVA), polyethyl hydroxyethyl cellulose, poly (2-ethyl) oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or a combination thereof.

In a particular embodiment, the ceramics can include calcium phosphate, hydroxyapatite, calcium sulfate, bioactive glass, or a combination thereof. In an alternative embodiment, the injectable biocompatible materials can include one or more fluids such as sterile water, saline, or sterile air.

In a particular embodiment, the hardness of the material used to inflate the exterior chamber 1902 can be less than or equal to the hardness of the material used to inflate the first interior chamber 1904 and the second interior chamber 1906, i.e., after the materials used to inflate the exterior chamber 1902, the first interior chamber 1904, and the second interior chamber 1906 are cured. Alternatively, the viscosity of the material used to inflate the exterior chamber 1902 can be less than or equal to the viscosity of the material used to inflate the first interior chamber 1904 and the second interior chamber 1906. In a particular embodiment, certain or all of the injected materials can be cured or cross-linked in situ to form a solid interspinous process brace with non-uniform bulk properties.

FIG. 21 indicates that a tether 2100 can be installed around the multi-chamber expandable interspinous process brace 1900, after the multi-chamber expandable interspinous process brace 1900 is expanded as described herein. As shown, the tether 2100 can include a proximal end 2102 and a distal end 2104. In a particular embodiment, the tether 2100 can circumscribe the multi-chamber expandable interspinous process brace 1900 and the spinous processes 2000, 2002. Further, the ends 2102, 2104 of the tether 2100 can be brought together and one or more fasteners can be installed therethrough to connect the ends 2102, 2104. Accordingly, the tether 2100 can be installed in order to prevent the distance between the spinous processes 2000, 2002 from substantially increasing beyond the distance provided by the multi-chamber expandable interspinous process brace 1900 after it is expanded and to maintain engagement of the interspinous processes with the spinous process pockets 1914, 1916, engagement structures 1920, 1922, or a combination thereof.

In a particular embodiment, the tether 2100 can comprise a biocompatible elastomeric material that flexes during installation and provides a resistance fit against the inferior process. Further, the tether 2100 can comprise a substantially non-resorbable suture or the like.

Description of a Method of Treating a Spine

Figure 22:
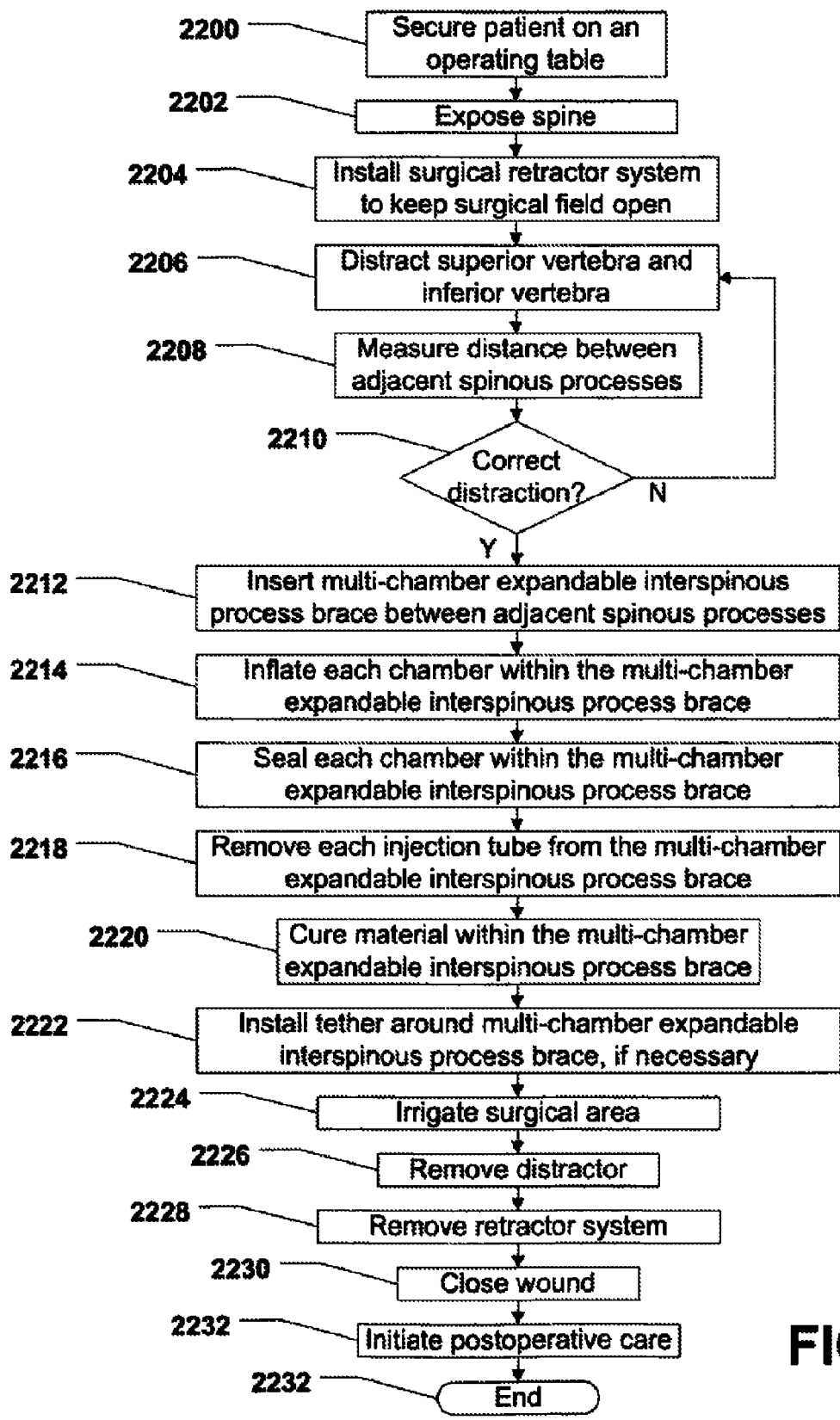
FIG. 22 is a flow chart illustrating a method of treating a spine.

Referring to FIG. 22, a method of treating a spine is shown and commences at block 2200. At block 2200, a patient can be secured on an operating table. Depending on the surgical approach to be used, the patient can be secured in a prone position for a posterior approach, a supine position for an anterior approach, a lateral decubitus position for a lateral approach, or another position well known in the art. At block 2202, the spine can be exposed in order to expose adjacent spinous processes. Further, at block 2204, a surgical retractor system can be installed to keep a surgical field open.

Moving to block 2206, a superior vertebra and inferior vertebra can be distracted. In a particular embodiment, the superior vertebra and inferior vertebra can be distracted using a distractor. At block 2208, a distance between the adjacent spinous processes can be measured. Thereafter, at block 2210 it is determined whether the distraction is correct, e.g., has the superior vertebra and inferior vertebral been distracted such that a distance between the adjacent spinous processes has reached a value that a surgeon has deemed therapeutic. For example, the superior vertebra and inferior vertebra can be distracted in order to reduce impingement on a nerve root.

If the distraction is not correct, the method can return to block 2206 and the superior vertebra and inferior vertebra can be further distracted. Conversely, if the distraction is correct, the method can move to block 2212 and a multi-chamber expandable interspinous process brace can be installed between a superior spinous process and an inferior spinous process. Thereafter, at block 2214, each chamber within the multi-chamber expandable interspinous process brace can be inflated.

Moving to block 2216, each chamber within the multi-chamber expandable interspinous process brace can be sealed. In a particular embodiment, each chamber within the multi-chamber expandable interspinous process brace can be sealed by curing the material within the each chamber of the multi-chamber expandable interspinous process brace. Alternatively, a plug, a dowel, or another similar device can be used to seal each chamber within the multi-chamber expandable interspinous process brace. Further, a one-way valve can be incorporated into each chamber of the multi-chamber expandable interspinous process brace and can allow material to be injected into each chamber of the multi-chamber expandable interspinous process brace, but prevent the same material from being expelled from each chamber of the multi-chamber expandable interspinous process brace.

At block 2218, each injection tube can be removed from the multi-chamber expandable interspinous process brace. Moreover, at block 2220, the material within one or more chambers of the multi-chamber expandable interspinous process brace can be cured. In a particular embodiment, the material within the multi-chamber expandable interspinous process brace can cure naturally, i.e., under ambient conditions, in situ. Alternatively, the material within one or more of the multi-chamber expandable interspinous process brace can be cured or crosslinked in situ using an energy source. For example, the energy source can be a light source that emits visible light, infrared (IR) light, or ultra-violet (UV) light. Further, the energy source can be a heating device, a radiation device, or other mechanical device. Alternatively or in addition, the material in one or more of the chambers can be crosslinked by introducing a chemical crosslinking agent into the chamber before removing the injection tube from the chamber.

Proceeding to block 2222, a tether can be installed around the multi-chamber expandable interspinous process brace. The tether can be installed in order to prevent a distance between the superior spinous process and the inferior spinous process from increasing substantially beyond the distance provided by the multi-chamber expandable interspinous process brace. At block 2224, the surgical area can be irrigated. At block 2226, the distractor can be removed. Also, at block 2228, the retractor system can be removed. Further, at block 2230, the surgical wound can be closed. The surgical wound can be closed by simply allowing the patient's skin to close due to the elasticity of the skin. Alternatively, the surgical wound can be closed using sutures, surgical staples, or any other suitable surgical technique well known in the art. At block 2232, postoperative care can be initiated. The method can end at state 2232.

CONCLUSION

With the configuration of structure described above, the multi-chamber expandable interspinous process brace provides a device that can be used to treat a spine and substantially alleviate or minimize one or more symptoms associated with disc degeneration, facet joint degeneration, or a combination thereof. For example, the multi-chamber expandable interspinous process brace can be installed between adjacent spinous processes in order to support the spinous processes and maintain them at or near a predetermined distance therebetween.

As described above, the multi-chamber expandable interspinous process brace can include two or three chambers. Alternatively, the multi-chamber expandable interspinous process brace can include four chambers, five chambers, six chambers, seven chambers, eight chambers, nine chambers, ten chambers, etc. Also, the chambers can be separate chambers, as described above, or the chambers can be interconnected to allow material to flow therebetween. The chambers can be inflated sequentially or simultaneously.

What is claimed is:

1. An expandable interspinous process spacer comprising:
   an outer chamber formed of an expandable material, the outer chamber having a generally H-shape in both a relatively smaller deflated configuration and a relatively larger inflated configuration, wherein the H-shape includes first and second spinous process-receiving notches;
   a theoretical axis extending from the first spinous process-receiving notch to the second spinous process-receiving notch;
   an inner expandable chamber disposed within and generally surrounded by the outer chamber, the inner expandable chamber disposed entirely on a first lateral side of the theoretical axis;
   the outer chamber being changeable from the relatively smaller deflated configuration to the relatively larger inflated configuration via injection of a first biocompatible material;
   the inner chamber changeable from a relatively smaller deflated configuration to a relatively larger inflated configuration via injection of a second biocompatible material; the inner chamber changeable from the deflated configuration to the inflated configuration independently of the outer chamber;
   wherein the spacer is configured to be disposed between adjacent first and second spinous processes such that the first spinous process-receiving notch receives the first spinous process and the second spinous process-receiving notch receives the second spinous process, and wherein when the spacer is disposed between the spinous processes the theoretical axis extends along a sagittal plane defined by the spinous processes.

2. The expandable spacer of claim 1 wherein the inner chamber is a first inner chamber and the spacer includes a second inner chamber and wherein when the spacer is disposed between the spinous processes, the second inner chamber is disposed entirely on a second opposing lateral side of the theoretical axis.

3. The expandable spacer of claim 2 further comprising a first injection tube operatively connected to the outer chamber, a second injection tube operatively connected to the first inner chamber, and a third injection tube operatively connected to the second inner chamber.

4. The expandable spacer of claim 1 further comprising the first biocompatible material disposed in the outer chamber and the second biocompatible material disposed in the inner chamber; wherein the first and second biocompatible materials are different.

5. The expandable spacer of claim 4 wherein the first biocompatible material is harder than the second biocompatible material.

6. The expandable spacer of claim 1 further comprising a tether having a length sufficient to wrap around an exterior of the outer chamber when the outer chamber is in the inflated configuration.

* * * * *